US008318768B2

(12) United States Patent
Dalence et al.

(10) Patent No.: US 8,318,768 B2
(45) Date of Patent: Nov. 27, 2012

(54) BRONCHODILATING ALPHA, BETA-UNSATURATED ISOQUINOLINE AMIDES

(75) Inventors: Maria Dalence, Lund (SE); Martin Johansson, Linhamn (SE); Viveca Thornqvist Oltner, Landskrona (SE); Jörgen Toftered, Lund (SE); David Wensbo, Billeberga (SE)

(73) Assignee: Respiratorius AB, Lund (SE)

( * ) Notice: Subject to any disclaimer, the term of this patent is extended or adjusted under 35 U.S.C. 154(b) by 255 days.

(21) Appl. No.: 12/668,599

(22) PCT Filed: Jul. 10, 2008

(86) PCT No.: PCT/EP2008/059001
§ 371 (c)(1),
(2), (4) Date: Jun. 15, 2010

(87) PCT Pub. No.: WO2009/007420
PCT Pub. Date: Jan. 15, 2009

(65) Prior Publication Data
US 2010/0256101 A1 Oct. 7, 2010

Related U.S. Application Data

(60) Provisional application No. 60/959,276, filed on Jul. 12, 2007, provisional application No. 61/005,742, filed on Dec. 7, 2007.

(30) Foreign Application Priority Data

Jul. 12, 2007 (SE) ...................................... 0701694

(51) Int. Cl.
*A61K 31/472* (2006.01)
*C07D 401/02* (2006.01)
*C07D 217/16* (2006.01)
(52) U.S. Cl. ........................................ 514/307; 546/146
(58) Field of Classification Search ........................ None
See application file for complete search history.

(56) References Cited

U.S. PATENT DOCUMENTS

| 5,932,573 A | 8/1999 | Yuen |
| 2005/0165004 A1 | 7/2005 | Skogvall et al. |
| 2009/0075978 A1 | 3/2009 | Huarand et al. |

FOREIGN PATENT DOCUMENTS

| DE | 10 2005 062987 | | 7/2007 |
| EP | 494623 | * | 7/1992 |
| EP | 0 514 851 | | 11/1992 |
| EP | 1 288 202 | | 3/2003 |
| JP | 5-239024 | | 9/1993 |
| WO | WO 97/23484 | | 7/1997 |
| WO | WO 98/15546 | | 4/1998 |
| WO | WO 98/17648 | | 4/1998 |
| WO | WO 98/18799 | | 5/1998 |
| WO | WO 98/27096 | | 6/1998 |
| WO | WO 99/28314 | | 6/1999 |
| WO | WO 01/96328 | | 12/2001 |
| WO | WO 02/00645 | | 1/2002 |
| WO | WO 03/037873 | | 5/2003 |
| WO | WO 03/037887 | | 5/2003 |
| WO | WO 2004/069830 | | 8/2004 |
| WO | WO 2005/005392 | | 1/2005 |
| WO | WO 2005/037214 | | 4/2005 |
| WO | WO 2005/060981 | | 7/2005 |
| WO | WO 2005/070887 | | 8/2005 |
| WO | WO 2005/092841 | | 10/2005 |
| WO | WO 2005/094554 | | 10/2005 |
| WO | WO 2005/095403 | | 10/2005 |
| WO | WO 2005/113510 | | 12/2005 |
| WO | WO 2006/012504 | | 2/2006 |
| WO | WO 2007/011290 | | 1/2007 |
| WO | WO 2009/007418 | | 1/2009 |
| WO | WO 2009/007419 | | 1/2009 |

OTHER PUBLICATIONS

Kubota et al, Bioorganic & Medicinal Chemistry (2004), 12(5), 871-882.*
West, Anthony R., Solid State Chemistry and its Applications, Wiley, New York, 1988, pp. 358 & 365.*
Accession Number: 1976:9050 CAPLUS, 1976.
Aldonyte et al. "Circulating monocytes from healthy indviduals and COPD patients." *Respiratory Research.* vol. 4. 2003. pp. 1-8.
Bobbit et al. "Synthesis of Isoquinolines. III. A new synthesis of 1,2,3,4-Tetrahydroisoquinolines." *New Synthesis.* vol. 30. 1965. pp. 2247-2250.
Bobbit et al. "Synthesis of Isoquinolines. VII. 4-Hydroxy-1,2,3,4-tetrahydroisoquinolines." *J. of Organic Chem.* vol. 33. No. 2. 1968. pp. 856-858.
Berglund et al. "SAR studies of capsazepinoid bronchodilators 3: The thiourea part (coupling region) and the 2-(4-chlorophenyl)ethyl moiety (C-region)." *Bioorganic & Medicinal Chem.* vol. 16. 2008. pp. 2529-2540.
Berglund et al. "SAR studies of capsazepinoid bronchodilators. Part 2: Chlorination and catechol replacement in the A-ring." *Bioorganic & Medicinal Chem.* vol. 16. 2008. pp. 2513-2528.
Fitzgerald et al. "Emerging trends in the therapy of COPD: bronchodilators as mono- and combination therapies." *Drug Discovery Today.* vol. 12. No. 11/12. 2007. pp. 472-478.
Gray et al. "Practical methylation of aryl halides by Suzuki-Miyaura coupling." *Tetrahedron Letters.* vol. 41. 2000. pp. 6237-6240.
Gunthorpe et al. "Identification and characterization of SB-366791, a potent and selectice vanilloid receptor (VR1/TRPV1) antagonist." *Neuropharmocology* vol. 46. 2004. pp. 133-149.
Dalence-Guzman et al. "SAR studies of capsazepinoid bronchodilators. Part 1: The importance of the catechol moiety and aspects of the B-ring structure." *Bioorganic & Medicien Chem.* vol. 16. 2008. pp. 2499-2512.
Hall et al. "Cytosporone E: racemic synthesis and preliminary antibacterial testing." *Bioorganic & Medicinal Chem.* vol. 13. 2005. pp. 1409-1413.

(Continued)

*Primary Examiner* — Zinna Northington Davis
(74) *Attorney, Agent, or Firm* — Merchant & Gould P.C.

(57) ABSTRACT

The invention relates to novel compounds having the general formula (I), and which compounds are useful to manufacture a medicament to treat a disorder or disease characterized by bronchoconstriction, e.g. COPD and asthma, and vasoconstriction, e.g. hypertension.

25 Claims, No Drawings

OTHER PUBLICATIONS

Marian et al. "Up-Regulated membrane and nuclear leukotriene B4 Receptors in COPD." *CHEST*. vol. 129. No. 6. 2006. pp. 1522-1530.

Matsuyama et al. "Effects of Omega-3 Polyunsaturated Fatty Acids on Inflammatory Markers in COPD." *CHEST*. vol. 128. No. 6. 2005. pp. 3817-3827.

Mongin et al. "Halogen Shuffling in Pyrides: Site Selective Electrophilic Sustitutions of 2-Chloro-6-(triflluoromethyl)pyridine." *Tetrahedron Letters*. vol. 39. 1998. pp. 1749-1752.

Okano et al. "Total Synthesis of (+)-Yatakemycin."*JACS*. vol. 128. 2006. pp. 7136-7137.

Profita et al. "Muscarinic receptors, leukotrien $B_4$ production and neutrophilic inflammation in COPD patients." *Allergy*. vol. 60. 2005. pp. 1361-1369.

Seggev et al. "Serum leukotrien B4 levels in patiens with obstructive pulmonary disease." *CHEST*. vol. 99. 1991. pp. 289-291.

Skogvall et al. "Discovery of a potent and long-acting bronchorelaxing capsazepinoid, RESPIR 4-95." *Pulmonary Pharmacology & Therapeutics*. vol. 21. 2008. pp. 125-133.

Skogvall et al. "Effects of capsazepine on human small airway responsiveness unravel a novel class of bronchorelaxants." *Pulmonary Pharmacology & Therapeutics*. vol. 20. 2007. pp. 273-280.

Stokker. "Preparation of 1,2,3,4-Tetrahydroisoquinolines Lacking electron donating groups—an intramolecular cyclization complementary to the pictet-spengler reaction." *Tetrahedron Letters*. vol. 37. No. 31. 1996. pp. 5453-5456.

Tofterred et al. "Synthesis of Chiral Macrocycles by Cyclodimerization of Diamines with Stepwise Nucleophilic Aromatic Substitution of 1,5-Difluoro-2,4-dinitrobenzene." *Synlett*. No. 14. 2004. pp. 2517-2520.

Tomaki et al. "Decreased expression of antioxidant enzymes and increased expression of chemokines in COPD lung." *Pulmonary Pharmacology & Therapeutics*. vol. 20. 2007. pp. 596.605.

Traves et al. Increased levels of the chemokins $GRO\alpha$ and MCP-1 in sputum samples from patients with COPD. *Thorax*. vol. 57. 2002. pp. 590-595.

Yokoyama et al. "Prototype Pictet-Spengler reactions catalyzed by superacids. Involvment of Dicationic Superelectrophiles." *J. Org. Chem*. vol. 64. 1999. pp. 611-617.

Friedman, "Future Treatment Strategies for COPD." *Clinical Cornerstone*. vol. 5. No. 1, Published 2003; pp. 45-51.

* cited by examiner

BRONCHODILATING ALPHA, BETA-UNSATURATED ISOQUINOLINE AMIDES

This application is a National Stage Application of PCT/EP2008/059001, filed 10 Jul. 2008, which claims benefit of Ser. No. 0701694-2, filed 12 Jul. 2007 in Sweden, U.S. Ser. No. 60/959,279, filed 12 Jul. 2007, and U.S. Ser. No. 61/005,742, filed 7 Dec. 2007 and which applications are incorporated herein by reference. To the extent appropriate, a claim of priority is made to each of the above disclosed applications.

FIELD OF THE INVENTION

The present invention relates to novel bronchorelaxing compounds, pharmaceutical compositions comprising such compounds, and a method of treating or alleviating conditions accompanied by bronchoconstriction and/or inflammation of the respiratory tract, and/or vasoconstriction, by use of such compounds.

BACKGROUND

Asthma and chronic obstructive pulmonary disease (COPD) are diseases affecting the respiratory system, which millions of people suffer from. These diseases are today regarded as inflammatory diseases and the symptoms comprise constriction of the airways. Common treatment of the associated bronchoconstriction involves use of beta-agonists, such as terbutalin and formoterol, and anticholinergics, such as ipratropium bromide and thiotropium bromide.

Hypertension, i.e. high blood pressure, increases the risk of stroke, heart attacks, heart failure and kidney disease. Medications presently used for the treatment of hypertension include the administration of beta-blockers, calcium channel blockers, diuretics, angiotensin-converting enzyme inhibitors and angiotensin II receptor antagonists. Vasoconstriction results in an increase in the blood pressure.

The treatments for prevention or reduction of bronchoconstricion, inflammation, such as inflammation of the respiratory tract, and vasoconstriction are in many ways insufficient and there is a need for alternative treatments.

SUMMARY

Accordingly, various embodiments of the present invention seek to mitigate, alleviate, circumvent or eliminate one or more of the above-identified deficiencies identified herein.

According to one aspect of the present invention, there is provided a compound of the general formula (I),

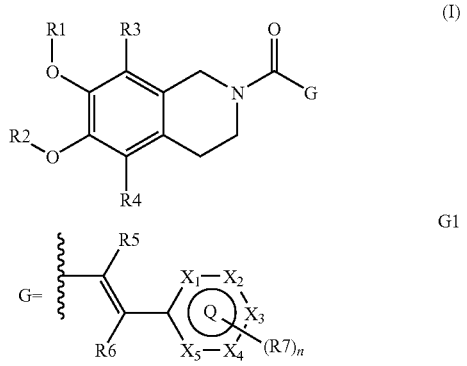

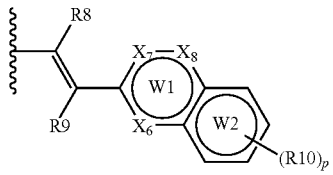

wherein R1 is selected from H and methyl; R2 is selected from H and methyl; R3 is selected from H, fluoro, chloro, bromo, C1-3 alkyl and CH2 phenyl; R4 is selected from H, fluoro, chloro, bromo, C1-3 alkyl and CH2 phenyl; G is selected from G1 and G2; in G1 the stereochemistry of the double-bond of G1, onto which the substituents R5 and R6 are attached, is such that R5 and R6 are oriented in a cis-fashion, or in a trans-fashion, relative to each other; R5 is selected from H, C1-5 alkyl, CH2 phenyl and C1-5 fluoroalkyl; R6 is selected from H, C1-5 alkyl, CH2 phenyl and C1-5 fluoroalkyl; X1, X2, X3, X4 and X5 are, independently of each other, selected from N and C; 0 (zero), 1 or 2 of X1, X2, X3, X4 and X5 is N; Q is optionally substituted with a maximum of "n" independently selected substituent(s) R7 at any substitutable ring carbon atom, wherein "n" represents an integer number; the integer number "n" is 0 to 2; R7 is selected from C1-5 alkyl, C1-5 fluoroalkyl, halo, hydroxy, C0-3 alkyleneOC0-5 alkyl, C0-3 alkyleneOC1-5 fluoroalkyl, C0-3 alkyleneNH2, C0-3 alkyleneNHC1-3 alkyl, C0-3 alkyleneN(C1-5 alkyl)2, in which the C1-5 alkyl may be the same or different, N(C4-5 alkylene), C1-5 alkylthio, S(O)C1-5 alkyl, SO2C1-5 alkyl, C1-5 fluoroalkylthio, NH(CO)C1-5 alkyl, NH(CO)C1-5 alkoxy, NHSO2C1-5 alkyl, (CO)C1-5 alkyl, COOH, (CO)C1-5 alkoxy, (CO)NH2, (CO)NHC1-5 alkyl, (CO)N(C1-5 alkyl)2, in which the C1-5 alkyl may be the same or different, cyano, SO2NHC0-5 alkyl, nitro, aryl, heteroaryl, azido (N3), and morpholinyl; in G2 the stereochemistry of the double-bond of G2, onto which the substituents R8 and R9 are attached, is such that R8 and R9 are oriented in a cis-fashion, or in a trans-fashion, relative to each other; R8 is selected from H, C1-5 alkyl, CH2 phenyl and C1-5 fluoroalkyl; R9 is selected from H, C1-5 alkyl, CH2 phenyl and C1-5 fluoroalkyl; the condensed rings W1 and W2 together represent a bicyclic aromatic system, in which X6, X7 and X8, independently of each other, are selected from N and C; none or one of X6, X7 and X8 is N; said bicyclic aromatic system is optionally substituted with a maximum of "p" independently selected substituent(s) R10, at any substitutable ring carbon atom of any of the rings W1 and W2, wherein "p" represents an integer number; the integer number "p" is 0 to 2; R10 is selected from C1-5 alkyl, C1-5 fluoroalkyl, halo, hydroxy, C0-3 alkyleneOC1-5 alkyl, C0-3 alkyleneOC0-5 fluoroalkyl, C0-3 alkyleneNH2, C0-3 alkyleneNHC1-3 alkyl, C0-3 alkyleneN(C1-5 alkyl)2, in which the C1-5 alkyl may be the same or different, N(C4-5 alkylene), C1-5 alkylthio, S(O)C1-5 alkyl, SO2C1-5 alkyl, C1-5 fluoroalkylthio, NH(CO)C1-5 alkyl, NH(CO)C1-5 alkoxy, NHSO2C1-5 alkyl, (CO)C1-5 alkyl, COOH, (CO)C1-5 alkoxy, (CO)NH2, (CO)NHC1-5 alkyl, (CO)N(C1-5 alkyl)2, in which the C1-5 alkyl may be the same or different, cyano, SO2NHC0-5 alkyl, nitro, aryl, heteroaryl, azido (N3), and morpholinyl; as a free base, an acid in its non-charged protonated form or a pharmaceutically acceptable salt, solvate or solvate of a salt thereof and as a pure stereoisomer, a racemic-, diastereomeric- or scalemic mixture; with the provisio that not both of R1 and R2 is methyl.

According to another aspect such a compound or a composition comprising such a compound may be used in medicine. Such compounds or compositions may also be used to manufacture a medicament.

According to another aspect a medicament comprising a compound according to formula I may be used to treat or prevent a disease or disorder of the respiratory apparatus characterized by bronchoconstriction. Furthermore, a medicament comprising a compound according to formula I may be used to treat or prevent a disease or disorder characterized by inflammation or vasoconstriction. Diseases and disorders, which compounds according to formula I may be used to treat comprise asthma, chronic obstructive pulmonary disease, which comprises chronic bronchitis and emphysema, bronchiectasis, cystic fibrosis, bronchiolitis or bronchopulmonary dysplasia.

According to another aspect a compound according to formula I or a medicament comprising such a compound, may also be used in a method to treat or prevent pulmonary disease characterized by bronchoconstriction. Such a method comprises the administration to a person in need of a bronchoconstriction relaxing dose of a compound according to formula I.

Further features of the invention are defined in the dependent claims and embodiments disclosed herein.

DETAILED DESCRIPTION OF THE INVENTION

Definitions

In the context of the present application and invention, the following definitions apply:

The term "addition salt" is intended to mean salts formed by the addition of a pharmaceutical acceptable acid, such as organic or inorganic acids, or a pharmaceutical acceptable base. The organic acid may be, but is not limited to, acetic, propanoic, methanesulfonic, benzenesulfonic, lactic, malic, citric, tartaric, succinic or maleic acid. The inorganic acid may be, but is not limited to, hydrochloric, hydrobromic, sulfuric, nitric acid or phosphoric acid. The base may be, but is not limited to, ammonia and hydroxides of alkali or alkaline earth metals. The term "addition salt" also comprises the hydrates and solvent addition forms, such as hydrates and alcoholates.

As used herein, "halo" or "halogen" refers to fluoro, chloro, bromo, and iodo.

As used herein, "alkyl" used alone or as a suffix or prefix, is intended to include both branched and straight chain saturated aliphatic hydrocarbon groups having from 1 to 12 carbon atoms or if a specified number of carbon atoms is provided then that specific number is intended. For example "C1-6 alkyl" denotes alkyl having 1, 2, 3, 4, 5 or 6 carbon atoms. When the specific number denoting the alkyl-group is the integer 0 (zero), a hydrogen-atom is intended as the substituent at the position of the alkyl-group. For example, "N(C0 alkyl)2" is equivalent to "NH2" (amino). Examples of alkyl include, but are not limited to, methyl, ethyl, n-propyl, i-propyl, n-butyl, i-butyl, sec-butyl, t-butyl, pentyl, and hexyl.

As used herein, "alkylenyl" or "alkylene" used alone or as a suffix or prefix, is intended to mean straight chain saturated aliphatic hydrocarbon groups having from 1 to 12 carbon atoms or if a specified number of carbon atoms is provided then that specific number is intended. For example "C1-6 alkylene" or "C1-6 alkylenyl" denotes "alkylene" or "alkylenyl" having 1, 2, 3, 4, 5 or 6 carbon atoms. When the specific number denoting the alkylenyl or alkylene-group is the integer 0 (zero), a bond is intended to link the groups onto which the alkylenyl or alkylene-group is substituted. For example, "NH(C0 alkylene)NH2" is equivalent to "NHNH2" (hydrazino). As used herein, the groups linked by an alkylene or alkylenyl-group are intended to be attached to the first and to the last carbon of the alkylene or alkylenyl-group. In the case of methylene, the first and the last carbon is the same. For example, "H2N(C2 alkylene)NH2", "H2N(C3 alkylene)NH2", "N(C4 alkylene)", "N(C5 alkylene)" and "N(C2 alkylene)2NH" is equivalent to 1,2-diamino ethane, 1,3-diamino propane, pyrrolidinyl, piperidinyl and piperazinyl, respectively.

Examples of alkylene or alkylenyl include, but are not limited to, methylene, ethylene, propylene, and butylene.

As used herein, "alkoxy" or "alkyloxy" is intended to mean an alkyl group as defined above with the indicated number of carbon atoms attached through an oxygen bridge. Examples of alkoxy include, but are not limited to, methoxy, ethoxy, n-propoxy, isopropoxy, n-butoxy, isobutoxy, t-butoxy, n-pentoxy, isopentoxy, cyclopropylmethoxy, allyloxy and propargyloxy. Similarly, "alkylthio" or "thioalkoxy" represent an alkyl group as defined above with the indicated number of carbon atoms attached through a sulphur bridge.

As used herein, "fluoroalkyl", "fluoroalkylene" and "fluoroalkoxy", used alone or as a suffix or prefix, refers to groups in which one, two, or three of the hydrogen(s) attached to any of the carbons of the corresponding alkyl, alkylene and alkoxy-groups are replaced by fluoro. Examples of fluoroalkyl include, but are not limited to, trifluoromethyl, difluoromethyl, fluoromethyl, 2,2,2-trifluoroethyl, 2-fluoroethyl and 3-fluoropropyl.

Examples of fluoroalkylene include, but are not limited to, difluoromethylene, fluoromethylene, 2,2-difluorobutylene and 2,2,3-trifluorobutylene.

Examples of fluoroalkoxy include, but are not limited to, trifluoromethoxy, 2,2,2-trifluoroethoxy, 3,3,3-trifluoropropoxy and 2,2-difluoropropoxy.

As used herein, the term "substitutable" refers to an atom to which a hydrogen is covalently attached, and to which another substituent may be attached instead of the hydrogen, directly or indirectly through synthesis. A non-limiting example of substitutable atoms include the carbon-atoms of pyridine. The nitrogen-atom of pyridine is not substitutable according to this definition.

As used herein, the term "aryl" refers to a ring structure, comprising at least one aromatic ring, made up of from 5 to 14 carbon atoms. Ring structures containing 5, 6, 7 and 8 carbon atoms would be single-ring aromatic groups, for example phenyl. Ring structures containing 8, 9, 10, 11, 12, 13, or 14 would be polycyclic, for example naphthyl. The aromatic ring may be substituted at one or more ring positions. The term "aryl" also includes polycyclic ring systems having two or more cyclic rings in which two or more carbons are common to two adjoining rings (the rings are "fused rings") wherein at least one of the rings is aromatic, for example, the other cyclic rings can be cycloalkyls, cycloalkenyls, cycloalkynyls, aryls and/or heterocyclyls. The terms ortho, meta and para apply to 1,2-, 1,3- and 1,4-disubstituted benzenes, respectively. For example, the names 1,2-dimethylbenzene and ortho-dimethylbenzene are synonymous.

As used herein, "heteroaryl" refers to a heteroaromatic heterocycle, having at least one ring with aromatic character, (e.g. 6 delocalized electrons) or at least two conjugated rings with aromatic character, (e.g. 4n+2 delocalized electrons where "n" is an integer), and comprising up to about 14 carbon atoms, and having at least one heteroatom ring member such as sulfur, oxygen, or nitrogen. Heteroaryl groups include monocyclic and bicyclic (e.g., having 2 fused rings)

systems. Examples of heteroaryl groups include without limitation, pyridyl (i.e., pyridinyl), pyrimidinyl, pyrazinyl, pyridazinyl, triazinyl, furyl (i.e. furanyl), quinolyl, tetrahydroquinolyl, isoquinolyl, tetrahydroisoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, benzimidazolyl, indolinyl, and the like.

As used herein, the term "substitutable" refers to an atom to which a hydrogen atom may be covalently attached, and to which another substituent may be present instead of the hydrogen atom. A non-limiting example of substitutable atoms include the carbon-atoms of pyridine. The nitrogen-atom of pyridine is not substitutable according to this definition. Further, according to the same definition, the imine nitrogen at position 3 in imidazole is not substitutable, while the amine nitrogen at position 1 is.

According to one embodiment of the present invention there is disclosed a compound according to formula (I)

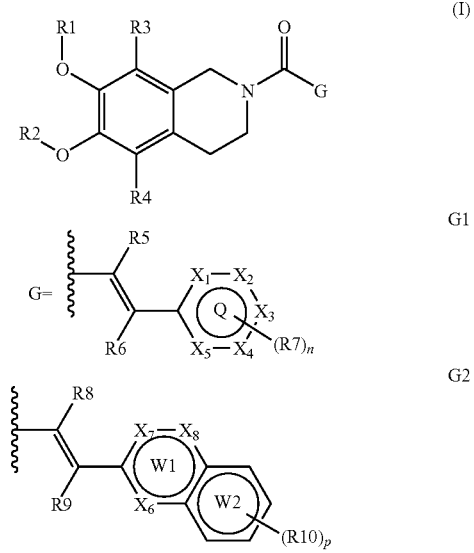

wherein R1 and R2 are, independently of each other, selected from H and methyl and at least one of them is H; R3 and R4 are, independently of each other, selected from H, fluoro, chloro, bromo, C1-3 alkyl and CH2 phenyl; G is selected from G1 to G2; the stereochemistry of the double-bond of G1, onto which the substituents R5 and R6 are attached, is such that R5 and R6 are oriented in a cis-fashion, or in a trans-fashion, relative to each other; R5 and R6 are, independently of each other, selected from H, C1-5 alkyl, CH2 phenyl and C1-5 fluoroalkyl; Q is selected from phenyl, i.e. all of X1, X2, X3, X4 and X5 are C, and nitrogen containing heteroaryl, such as pyridyl and pyrimidinyl, i.e. X1, X2, X3, X4 and X5 are, independently of each other, selected from N and C and no more than two of X1, X2, X3, X4 and X5 are N, the residue being C; Q is optionally substituted with a maximum of "n" independently selected substituent(s) R7 at any substitutable ring carbon atom; "n" represent an integer number of 0, 1 or 2, i.e. if "n" is 0, then Q is unsubstituted; R7 is selected from C1-5 alkyl, C1-5 fluoroalkyl, halo, hydroxy, C0-3 alkyleneOC0-5 alkyl, C0-3 alkyleneOC1-5 fluoroalkyl, C0-3 alkyleneNH2, C0-3 alkyleneNHC1-3 alkyl, C0-3 alkyleneN(C1-5 alkyl)2, N(C4-5 alkylene), C1-5 alkylthio, S(O)C1-5 alkyl, SO2C1-5 alkyl, C1-5 fluoroalkylthio, NH(CO)C1-5 alkyl, NH(CO)C1-5 alkoxy, NHSO2C1-5 alkyl, (CO)C1-5 alkyl, COOH, (CO)C1-5 alkoxy, (CO)NH2, (CO)NHC1-5 alkyl, (CO)N(C1-5 alkyl)2, cyano, SO2NHC0-5 alkyl, nitro, aryl, heteroaryl, azido (N3), and morpholinyl; the stereochemistry of the double-bond of G2, onto which the substituents R8 and R9 are attached, is such that R8 and R9 are oriented in a cis-fashion, or in a trans-fashion, relative to each other; R8 and R9 are, independently of each other, selected from H, C1-5 alkyl, CH2 phenyl and C1-5 fluoroalkyl; the condensed rings W1 and W2 together represent a bicyclic aromatic system, wherein X6, X7 and X8 are, independently of each other, selected from N and C and no more than one of X6, X7 and X8 are N, the residue being C; said bicyclic aromatic system is optionally substituted with a maximum of "p" independently selected substituent(s) R10, at any substitutable ring carbon atom of any of the rings W1 and W2; "p" represents an integer number of 0, 1 or 2, i.e. if "p" is 0, then W1 and W2 is unsubstituted; R10 is selected from C1-5 alkyl, C1-5 fluoroalkyl, halo, hydroxy, C0-3 alkyleneOC0-5 alkyl, C0-3 alkyleneOC1-5 fluoroalkyl, C0-3 alkyleneNH2, C0-3 alkyleneNHC1-3 alkyl, C0-3 alkyleneN(C1-5 alkyl)2, N(C4-5 alkylene), C1-5 alkylthio, S(O)C1-5 alkyl, SO2C1-5 alkyl, C1-5 fluoroalkylthio, NH(CO)C1-5 alkyl, NH(CO)C1-5 alkoxy, NHSO2C1-5 alkyl, (CO)C1-5 alkyl, COOH, (CO)C1-5 alkoxy, (CO)NH2, (CO)NHC1-5 alkyl, (CO)N(C1-5 alkyl)2, cyano, SO2NHC0-5 alkyl, nitro, aryl, heteroaryl, azido (N3), and morpholinyl, such as N-morpholinyl;

A compound according to formula (I) as disclosed above may be present as a free base, an acid in its non-charged protonated form or a pharmaceutically acceptable addition salt, solvate or solvate of a salt thereof.

Further a compound according to formula (I) as disclosed herein may be present as pure stereoisomer, a racemic-, diastereomeric- or scalemic mixture.

As disclosed below, various embodiments of the present invent are drawn to compounds according to the general formula (I), as disclosed above, wherein the various generic groups (R1 to R10, X1 to X8, Q, W1 and W2) as well as the integers "n" and "p" are elaborately disclosed.

As disclosed above, at least one of R1 and R2 should be hydrogen in formula (I). Compounds, in which at least one of R1 and R2 is hydrogen was shown to be more potent, in at least one of the herein described in-vitro methods, than the corresponding di-methoxy derivatives. In one embodiment both R1 and R2 are hydrogen.

In one embodiment R3 and R4 are, independently of each other, selected from H, fluoro, chloro, bromo, and methyl. In another embodiment they are independently of each other, selected from H, chloro and bromo, more preferred from chloro and bromo and particularly preferred from chloro. In one embodiment R3 and R4 may also both be H.

In another embodiment both R3 and R4 are the same and are selected from H, fluoro, chloro, bromo, and methyl. In another embodiment they are selected from H, chloro and bromo, more preferred from chloro and bromo. One advantage of a compound wherein R3 is identical to R4 is, among others, that the purification of synthetic intermediates to produce such a compound is easier.

In another embodiment G is G1 and the stereochemistry of the double-bond of G1, onto which the substituents R5 and R6 are attached, is such that R5 and R6 are oriented in a trans-fashion relative to each other. In an embodiment wherein G is G1, R5 and R6 may be, independently of each other, selected from H, C1-5 alkyl, such as methyl, CH2 phenyl and C1-5 fluoroalkyl, such as CF3. R5 and R6 may also be, independently of each other, selected from H and methyl. Further, R5 may be H or Me, such as being H. Also R6 may be H or Me, such as being H.

In another embodiment G is G1 and Q is phenyl, i.e. X1 to X5 are C.

In another embodiment G is G1 and at least one of X1 to X5 is N. Further two of X1 to X5, such as X1 and X3 or X1 and X5, may be N and the residue being C.

In another embodiment G is G1 and Q is pyridyl, i.e. one of X1 to X5 are N and the residue being C. In an embodiment wherein Q is pyridyl, it is preferred if X1 or X2 is N.

In another embodiment G is G1, "n" is 1 or 2 and R7 is, independently of each other if "n" is 2, selected from C1-C3 alkyl, such as methyl, trifluoromethyl, halo, such as fluoro and chloro, hydroxy, N(C4-5 alkylene), methoxy, SO2Me, cyano, thienyl, nitro, phenyl, morpholinyl, such as N-morpholinyl, and N(C1-3 alkyl)2, in which the C1-3 alkyl may be the same or different, such as N(Me)2. In another embodiment G is G1, "n" is 1 or 2 and R7 may be, independently of each other if "n" is 2, selected from methyl, trifluoromethyl, hydroxyl, fluoro, chloro and N(C5 alkylene). In another embodiment wherein G is G1, "n" may be 1 or 2 and R7 may be, independently of each other if "n" is 2, selected from trifluoromethyl, fluoro, chloro, NMe2 and methyl.

In one embodiment at least one R7 is a heteroaryl, such as 5- or 6-membered heteroaryl. In another embodiment at least one R7 is a 5-membered heteroaryl, such as a thienyl.

In an embodiment wherein G is G1 and "n" is 1 or 2, one substituent R7 may be positioned at X3.

In an embodiment wherein G is G1 and "n" is 2, one substituent R7 may positioned at X3 and the other at X1 or X5.

In another embodiment G is G1 and "n" is 0 (zero), i.e. Q is unsubstituted.

In another embodiment G is G2 and the stereochemistry of the double-bond of G1, onto which the substituents R8 and R9 are attached, is such that R8 and R9 are oriented in a trans-fashion relative to each other. In an embodiment wherein G is G2, R8 and R9 may be, independently of each other, selected from H and methyl.

In another embodiment G is G2 and at least one of X6, X7 and X8 is N, the residue being C. In an embodiment wherein G is G2, one of X6, X7 and X8 may be N. If at least one of X6, X7 and X8 is N, then it is preferred if X8 is N. Similarly, it is preferred if X8 is N if one of X6, X7 and X8 is N.

In another embodiment G is G2, "n" is 1 or 2 and R10 is, independently of each other if "n" is 2, selected from C1-C3 alkyl, such as methyl, trifluoromethyl, halo, such as fluoro and chloro, hydroxy, N(C4-5 alkylene), methoxy, SO2Me, cyano, thienyl, nitro, phenyl, morpholinyl, such as N-morpholinyl and N(C1-3 alkyl)2, in which the C1-3 alkyl may be the same or different, such as N(Me)2. In another embodiment G is G2, "n" is 1 or 2 and R10 may be, independently of each other if "n" is 2, selected from methyl, trifluoromethyl, hydroxyl, fluoro, chloro and N(C5 alkylene). In another embodiment G is G2, "n" is 1 or 2 and R10 is, independently of each other if "n" is 2, selected from methyl, trifluoromethyl, NMe2, fluoro and chloro.

In another embodiment G is G2 and "n" is 0 (zero), i.e. W1 and W2 are unsubstituted.

In another embodiment, a compound according to the invention is selected from the group consisting of:

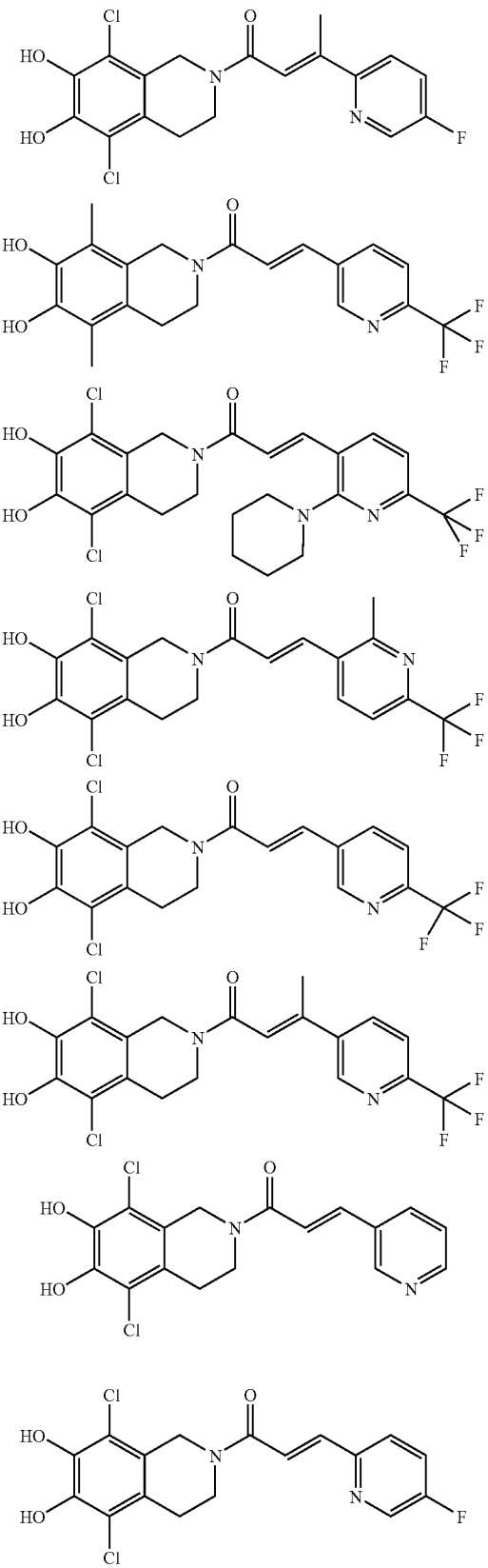

-continued

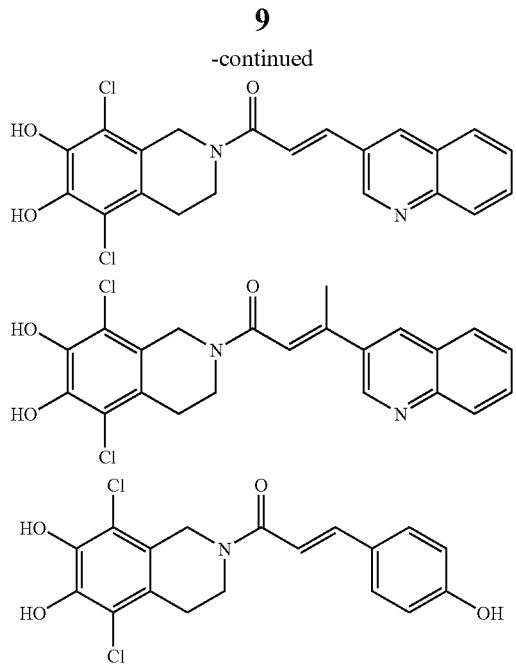

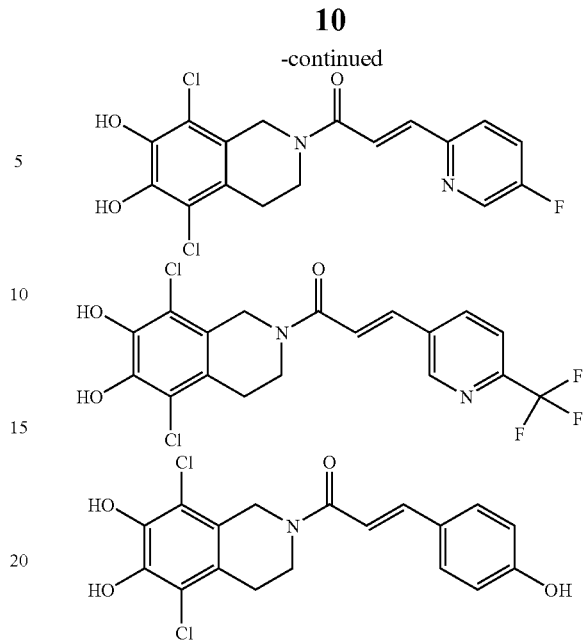

In another embodiment, a compound according to the invention is selected from the group consisting of:

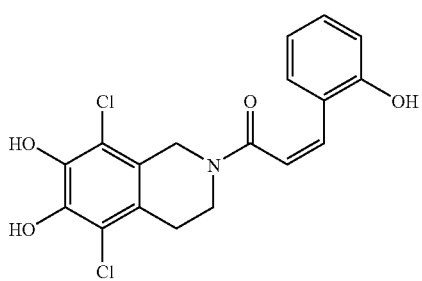

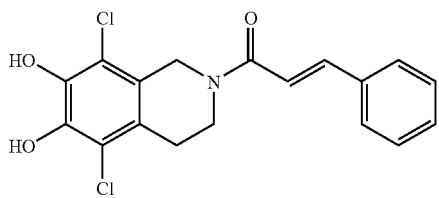

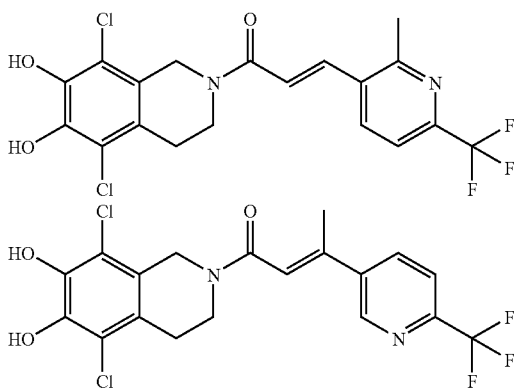

A compound according to formula (I) may be used in therapy. It may be used to treat, revoke, mitigate, alleviate or prevent a disease or condition characterized by bronchoconstriction of the respiratory apparatus of a mammal, such as a human being. Further it might be used to treat, revoke, mitigate, alleviate or prevent a disease or condition characterized by inflammation or vasoconstriction of the respiratory apparatus, or other organs or parts of the body, of a mammal, such as a human being. A method to treat, revoke, mitigate, alleviate or prevent bronchoconstriction in a mammal, such as a human being, in need thereof is also disclosed. Furthermore a method to treat, revoke, mitigate, alleviate or prevent inflammation or vasoconstriction of the respiratory apparatus, or other organs or parts of the body, of a mammal, such as a human being, in need thereof is also disclosed. Such method includes the administration of therapeutically effective amount of a compound according to formula (I). Furthermore a compound according to formula (I) may be used for the prevention and/or treatment of a disease or condition selected from the group consisting of asthma, chronic obstructive pulmonary disease, chronic bronchitis, emphysema, bronchiectasis, cystic fibrosis, bronchiolitis and bronchopulmonary dysplasia Additionally, a compound according to formula (I) may be used to manufacture a medicament, such as pharmaceutical composition. Such a medicament may be useful to treat, revoke, mitigate, alleviate or prevent a disease or condition characterized by bronchoconstriction of the respiratory apparatus of a mammal, such as a human being. It may also be useful to treat, revoke, mitigate, alleviate or prevent a disease or condition characterized by inflammation or vasoconstriction of the respiratory apparatus or other organs or parts of the body of a mammal, such as a human being. A molecule according to formula (I) may further be used to manufacture a medicament for the prevention and/or treatment of asthma, chronic obstructive pulmonary disease, chronic bronchitis, emphysema, bronchiectasis, cystic fibrosis, bronchiolitis and bronchopulmonary dysplasia.

When used in herein, "prevent/preventing" should not be construed to mean that a condition and/or a disease never might occur again after use of a compound or medicament according to embodiments disclosed herein to achieve prevention. Further, the term should neither be construed to mean that a condition not might occur, at least to some extent, after such use to prevent said condition. Rather, "prevent/preventing" is intended to mean that the condition to be prevented, if occurring despite such use, will be less severe than without such use.

The usefulness of the compounds, as defined in the preceding embodiments, in treating, pretreating, revoking, mitigating, alleviating and/or preventing a condition of the respiratory apparatus characterized by bronchoconstriction, were evaluated in a complex and relevant in vitro model. The in vitro model was in accordance with the in vitro model disclosed in US 2006-0040254 A1 and by Skogvall, S., Berglund, M., Dalence-Guzman, M. F., Svensson, K., Jonsson, P., Persson, C. G. A and Sterner, O., in Pulmonary Pharmacology and Therapeutics, vol 20:3, 2007, p. 273-280. All references disclosed herein are hereby incorporated in their entirety by reference.

In short, lung tissue was obtained from patients undergoing lobectomia or pulmectomia due to lung carcinoma. From the bronchus of this tissue were rectangular oblong preparations obtained. The contraction induced by inflammatory mediators, such as Leukotriene D4, histamine, prostaglandin D2 or acetylcholine, in the presence and absence of the compound to be evaluated, were compared.

Capsazepine, one of the first reported TRPV1-antagonists, has been shown to have an effect of human airways (Skogvall, S., Berglund, M., Dalence-Guzman, M. F., Svensson, K., Jonsson, P., Persson, C. G. A and Sterner, O., Pulmonary Pharmacology and Therapeutics, vol 20:3, 2007, p. 273-280), but is also known to posses a range of other biological effects. Consequently capsazepine is not selective towards one target and accordingly its usefulness as a molecular tool has been questioned (Gunthorpe, M. J., Neurpharmacology, 2004, 46, 133).

According to one embodiment, preferred compounds according to any of the embodiments disclosed herein are those being at least comparably active to Capsazepine, in the in vitro model referred to herein.

According to another embodiment, preferred compounds according to any of the embodiments disclosed herein are those being at least comparably active to Res-4-95, disclosed in Pulmonary Pharmacology & Therapeutics, 2007, 21(1), 125-133 as a potent analogue to Capsazepine, in the in vitro model referred to herein.

Inflammation is closely associated with COPD. New drugs that reduce pulmonary inflammation by modulation of inflammatory pathways involving inflammatory mediators, such as leukotriene B4 (LTB4) and monocyte chemotactic protein-1 (MCP-1), is believed to provide effective and disease-modifying therapies and is therefore much desired (Friedman et al, Clinical Cornerstone, 2003, 5, 45-51).

MCP-1 attracts monocytes that can differentiate into macrophages. Macrophages are generally believed to be responsible for the continued protolytic activity in the lungs of COPD-patients, as well as driving the inflammatory process in the same by recruitment of neutrophils. The fact that increased levels of various inflammatory mediators, or associated receptors, correlates with the diagnosis of COPD, is indicative of their relevance in disease severity and progression. Comparative studies between COPD-patients and non-COPD subjects have, for example, shown that the former group has increased levels of MCP-1 in the sputum (Traves, L. S. et al, Thorax, 2002, 57, 590-595), increased mRNA expression of MCP-1 in lung tissue (Tomaki, M. et al, Pulmonary Pharmacology & Therapeutics, 2007, 20, 596-605), and increased lipopolysaccharide (LPS) stimulated release of MCP-1 from isolated blood monocytes (Aldonyte, R. et al, Respiratory Research, 2003, http://respiratory-research.com/content/4/1/11).

LTB4 is an aracidonic acid metabolite involved in leukocyte recruitment. LTB4 is a potent chemoattractant and activator for neutrophils. The LTB4-receptors BLT1 and PPAR are upregulated in peripheral lung of COPD patients (Marian, E. et al, 2006, 129, 1523-1530). Higher sputum—(Profita, M. et al, Allergy, 2005, 60, 1361-1369) and serum—(Segger, J. S. et al, Chest, 1991, 99, 289-291) concentrations of LTB4 is found in COPD-patients as compared to healthy controls. Reduction of serum inflammatory mediator levels, including LTB4-levels, by a dietary supplement containing omega-3 polyunsaturated fatty acids, correlated significantly to a clinical improvement in COPD-patients (Matsuyama, W. et al, Chest, 2005, 128, 3817-3827).

Accordingly, the anti-inflammatory effect, i.e. the usefulness in treating, pretreating, revoking, mitigating, alleviating and/or preventing an inflammation, such as an inflammation of the airways, of the compounds, as defined in the embodiments herein, may be assessed in an in vitro human peripheral blood mononuclear cell (PBMC) model. Further, the anti-inflammatory effect may be compared to the effect of dexamethasone, a known potent anti-inflammatory glucocorticoid.

According to one embodiment, preferred compounds according to any of the preceding embodiments are those being at least comparably active to dexamethaonse in such an anti-inflammatory in-vitro model.

A medicament, e.g. a pharmaceutical composition, as has been described herein above may further comprise pharmaceutically acceptable carriers, diluents, stabilisers and/or excipients.

"Pharmaceutically acceptable" means a carrier, stabiliser, diluent, excipient or other constituents that, at the dosage and concentrations employed, does not cause any unwanted effects in the patients to whom it is administered. Such pharmaceutically acceptable carriers, stabilisers, dilutents or excipients are well-known in the art, and examples of such are for example disclosed in Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

A medicament according to embodiments herein maybe administered to a patient in a pharmaceutically effective dose. By "pharmaceutically effective dose" is meant a dose that is sufficient to produce the desired effects in relation to the condition for which it is administered. The exact dose may depend on the activity of the compound, manner of administration, nature and severity of the disorder and/or disease and the general conditions, such as age and body weight of the patient.

According to one embodiment, a medicament according embodiments herein may be administered alone or in combination with other therapeutic agents, such as anti-asthmatics. These agents may be incorporated as part of the same medicament or may be administered separately. It is well known in the art that a combination of mechanistically unrelated therapeutic agents in the same medicament may have beneficial effects in the treatment of conditions or diseases characterized by bronchoconstriction, as described in, for example, M. F. Fitzgerald and J. C. Fox, Drug Discovery Today, 2007, 12 (11/12), p. 472-478.

In one embodiment of the invention such other therapeutic agents to be administered in combination with a medicament according to embodiments of the invention are selected from therapeutic agents known to the one skilled in the art to prevent bronchoconstriction or revoke, fully or partly, any present bronchoconstriction. Examples of such agents are, but not limited to, β2-agonists, anticholinergics calcium antagonists, and other agents suitable for the treatment of asthma and/or COPD and related diseases and/or disorders. Preferred agents in this aspect are β2-agonists and anticholinergics. Furthermore such other therapeutic agents to be administered in combination with the medicament of the invention may also comprise therapeutic agents known to the one skilled in the art to be useful to treat, revoke, mitigate, alleviate or prevent inflammation associated with diseases and disorders of respiratory tract. Examples of such agents are corticosteroids.

When a compound according to embodiments disclosed herein is combined with at least another therapeutic agent, such as an anti-asthmatic, in a medicament, such as a pharmaceutical composition, a therapeutically effective dose of said medicament may comprise 1 to 10 times less than the respective established therapeutically effective dose of the components, i.e. a compound according to embodiments disclosed herein and the therapeutic agent, when administrated alone for prevention or treatment of the same disease or condition of each. Accordingly, by combining a compound according to the present invention with another therapeutic agent, such as an anti-asthmatic, it may be possible to achieve synergistic effects compared to if only a compound according to the present invention, or the other therapeutic agent, were administrated alone. Furthermore, it may be possible to improve both the underlying cause, e.g. the inflammation, and the clinical signs, e.g. airflow obstruction and exacerbations.

A method to treat, revoke, mitigate, alleviate or prevent bronchoconstriction and/or an inflammatory condition in a mammal, such as a human being, in need thereof, by the administration of a compound or medicament, such as a pharmaceutical composition, according to embodiments disclosed herein may also include the simultaneous or consecutive administration a therapeutic agent, such as an anti-asthmatic. In such a method the therapeutically effective dose of said compound, medicament or pharmaceutical composition and said therapeutic agent may comprise 1 to 10 times less than the respective established therapeutically effective dose when administered alone for prevention or treatment of the same disease or condition. The advantageous of such co-administration are discussed above.

A medicament according to embodiments disclosed herein may be administered through different routes such as, but not limited to, intravenously, intraperitonealy, intramuscularly, intranasaleously, subcutaneously, sublingually, rectally, orally or through inhalation or insufflation.

Particular suitable formulations of the medicament of the invention are formulations suitable to be taken orally or to be administrated through inhalation or insufflation.

Administration by inhalation or insufflation will allow a high proportion of the delivered dose to reach the site of action, that is, the bronchi and the lung in general. Furthermore the systemic effects may be lower if the medicament is administrated through inhalation or insufflation compared to other administration routes.

Inhalation may be by the oral or the nasal route. Conventional pulmonary applicators may be employed, such as pressurized spray containers comprising suitable propellants for aerosols and powder spray devices for preparations in form of fine powders. Pharmaceutical compositions suitable for administration by the inhalation or insufflation route are known in the art. The compound may be dissolved in a suitable vehicle or employed as a fine powder, such as a micronized powder of a particle size from about 2 μm to about 20 μm. An indicated daily dose for administration by inhalation may be 10 times and more lower than the corresponding oral dose. Satisfactory doses, preferably metered by using a device capable of metering, or by single doses of predetermined size, may easily be determined by experimentation.

Compounds according to embodiments of the present invention may also be useful in treatment or prevention of hypertension. In the treatment of conditions or diseases characterized by hypertension, by employment of the compounds of the present invention, oral administration is the preferred route of administration.

In addition to their use in therapeutic medicine, compounds according to formula I may also be useful as pharmacological tools in the development and standardisation of in vitro and in vivo test systems for the evaluation of other compounds with similar activity. Furthermore, compounds of formula I may be used as molecular probes to identify and/or locate the target of their action, such as a target within the airways, as well as employed as a diagnostic tool for diagnosis of a disease or condition in vivo, ex vivo or in vitro, or as synthetic precursors to such probes. Molecular probes of formula I may include reactive, labeled, i.e. compounds of formula I wherein one or several of the composing atoms have been enriched with a radioactive or by other means detectable isotope, and fluorescent compounds as well known to the one skilled in the art.

Methods of Preparation

Other embodiments of the present invention relates to processes for preparing a compound according to formula I as a free base, acid, or salts thereof. Further, additionally embodiments relate to synthetic intermediates, which are useful in the synthesis of a compound of formula I as a free base, acid, or salts thereof. Specific and generic examples of such intermediates are given below. Further, such intermediates may include compounds according to formula I, which may be used to produce another compound according to formula I.

Throughout the following description of such processes it is to be understood that, where appropriate, suitable protecting groups will be attached to, and subsequently removed from, the various reactants and intermediates in a manner that will be readily understood by one skilled in the art of organic synthesis. Conventional procedures for using such protecting groups, as well as examples of suitable protecting groups, are well known within the art. Further such procedures and groups are described in the literature, such as in "Protective Groups in Organic Synthesis", 3rd ed., T. W. Green, P. G. M. Wuts, Wiley-Interscience, New York (1999).

It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis.

Examples of transformations are given below, and it is to be understood that the described transformations are not limited only to the generic groups or substituents for which the transformations are exemplified.

References and descriptions on other suitable transformations are for example given in "Comprehensive Organic Transformations—A Guide to Functional Group Preparations", 2nd ed., R. C. Larock, Wiley-VCH, New York (1999). References and descriptions of other suitable reactions are described in textbooks of organic chemistry well known to the one skilled in the art, such as "March's Advanced Organic Chemistry", 5th ed., M. B. Smith, J. March, John Wiley & Sons (2001) or, "Organic Synthesis", 2nd ed., M. B. Smith, McGraw-Hill, (2002).

Techniques for purification of intermediates and final products include for example, straight and reversed phase chromatography on column or rotating plate, recrystallisation, distillation and liquid-liquid or solid-liquid extraction, which will be readily understood by the one skilled in the art.

The terms "room temperature" and "ambient temperature" shall mean, unless otherwise specified, a temperature between 16 and 25° C. The term "reflux" shall mean, unless otherwise stated, in reference to an employed solvent using a temperature at or slightly above the boiling point of the named solvent. It is understood that microwaves can be used for the heating of reaction mixtures.

The terms "flash chromatography" or "flash column chromatography" shall mean preparative chromatography on silica using an organic solvent, or mixtures thereof, as mobile phase.

Abbreviations
aq. aqueous;
CDI 1,1'-carbonyl diimidazole;
CH$_2$Cl$_2$ dichloromethane;
DABCO 1,4-diazabicyclo[2.2.2]octane;
DMAP 4-dimethylaminopyridine;
DMF N,N-dimethylformamide;
DMSO dimethyl sulfoxide;
EDC.HCl N-(3-dimethylaminopropyl)-N'-ethyl-carbodiimide;
Et$_3$N triethylamine;
EtOAc ethyl acetate;
EtOH ethanol;
Et2O diethylether;
h hour(s);
HBr hydrogen bromide;
HCl hydrogen chloride;
HOBt 1-hydroxybenzotriazole hydrate;
K$_2$CO$_3$ potassium carbonate;
ma major;
MeOH methanol;
MgSO$_4$ magnesium sulphate;
mi minor;
NaHCO$_3$ sodium bicarbonate;
NaOH sodium hydroxide;
Pet. Ether petroleum ether;
r.t. or rt room temperature;
rot. mix. rotameric mixture
sat. saturated;
THF tetrahydrofurane;
TLC thin layer chromatography;
TMS tetramethylsilane.

Methods of Preparation of Final Compounds of Formula I by Coupling of intermediates II and III (Scheme 1)

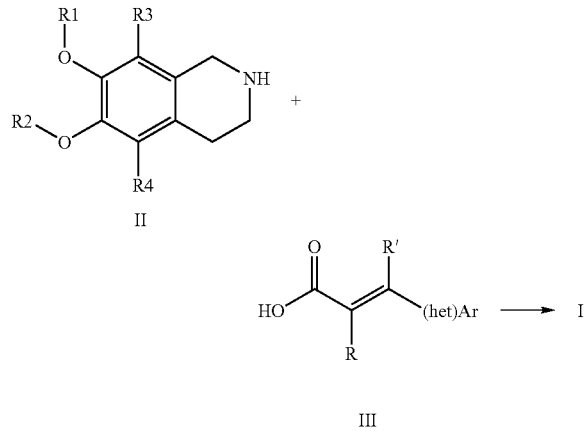

Formation of compounds of formula I, may be accomplished by coupling of II and III (wherein depicted "(het)Ar" is represented by aryl or heteroaryl, R corresponds to R5 and R8 of formula I, R' corresponds to R6 and R9 of formula I) under standard amide coupling conditions, such as in the presence of N-(3-dimethylaminopropyl)-N'-ethyl-carbodiimide hydrochloride, 1-hydroxybenzotriazole hydrate, 4-dimethylaminopyridine and caesium carbonate (see for example Toftered et al., SYNLETT, 2004, 2517-2520), or, for example, via initial conversion of the acid III into the corresponding acid chloride, followed by coupling with II according to standard protocols. The N-acylation of II may be accompanied by competing O-acylation when one or both of the substituents R1 and R2 are hydrogens. Thus, it is preferred to protect the corresponding phenolic moieties with suitable protective groups, such as methyl, before N-acylation of II. Methyl protective groups may be introduced by treatment with a methyl halide in the presence of a base according to standard procedures, and removed after the N-acylation by treatment with, for example, hydrogen bromide or boron tribromide (Hall et al., Bioorg. Med. Chem., 2005, 13, 1409-1413). Other aromatic methyl ethers, optionally present in the molecule, are then simultaneously cleaved off.

Methods of preparation of intermediates of formula II (Scheme 2)

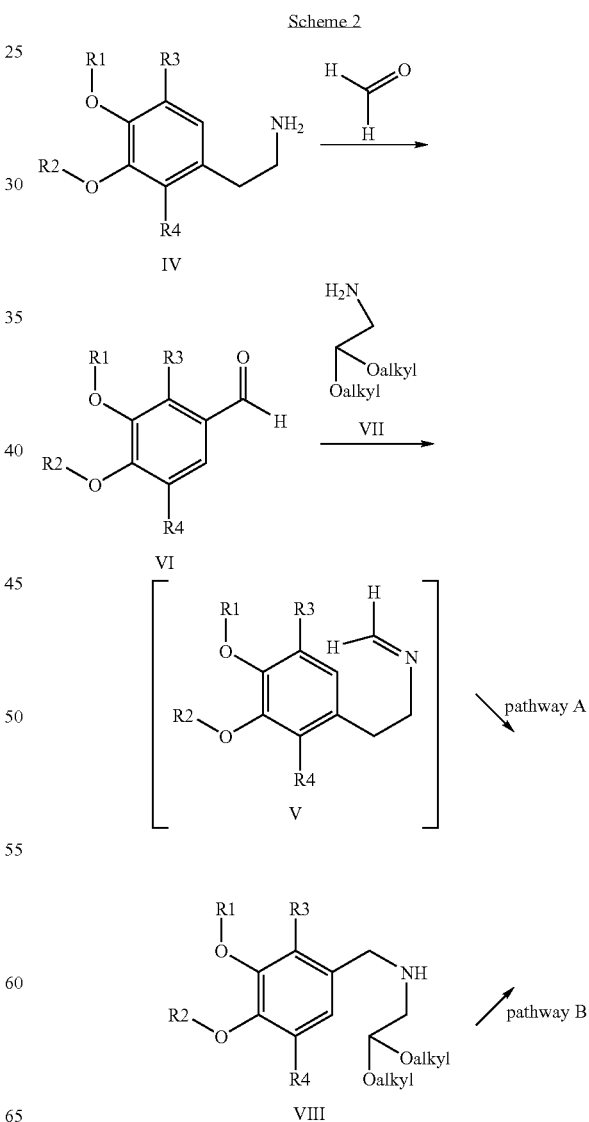

Examples of two non-limiting methods for the preparation of intermediates of formula II, by assembly of the tetrahydroisoquinoline ring, include pathway A and pathway B.

The synthesis according to pathway A involves a Pictet-Spengler reaction in which readily available phenylethylamine IV is reacted with formaldehyde to yield V, followed by cyclisation under acidic conditions (Yokoyama et al., J Org Chem, 1999, 64, 611-617; for a modified procedure allowing cyclisation onto electron poor aromatics see for example Stokker et al., Tetrahedron Lett, 1996, 37, 5453-5456).

The synthesis corresponding to pathway B involves a Pomerantz-Fritsch reaction under reductive conditions in which readily available benzaldehydes VI are reacted with aminoacetales VII (depicted "alkyl" is preferably short alkyls such as ethyl) to yield VIII, followed by cyclisation under acidic and reductive conditions to yield II (see for example: Bobbit et al., J Org Chem, 1965, 30, 2247-2250; Bobbit et al., J Org Chem, 1968, 33, 856-858).

Additional methods for the preparation of intermediates II include, for example, the direct introduction of the substituents R3 and R4 by electrophilic aromatic substitution, such as chlorination by treatment with sulphuryl chloride in acetic acid, or bromination as described in Okano et al., Tetrahedron, 2006, 128, 7136-7137.

Methods of Preparation of Intermediates of Formula III (Scheme 3)

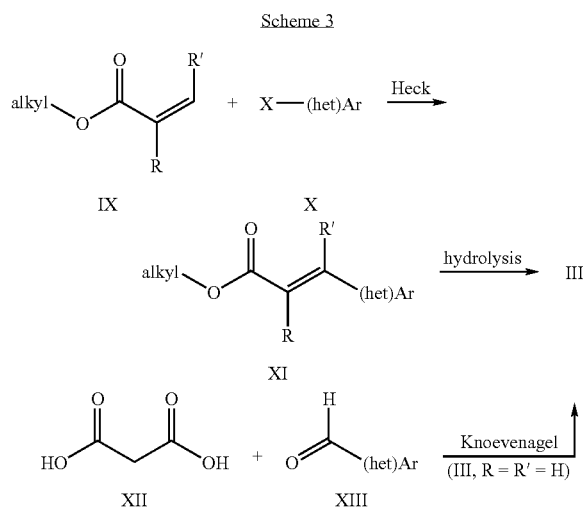

Intermediates of formula III may be prepared from readily available esters IX (depicted "alkyl" is preferably short alkyls such as methyl) by, for example, standard palladium catalyzed Heck-coupling with aryl- and heteroaryl-halides X (depicted X is iodo, bromo or chloro), followed by hydrolysis with, for example, sodium hydroxide in a mixture of THF and ethanol. The suitable reaction conditions, and the type of palladium catalyst employed in the Heck-coupling, is much dependant on the nature of the substituent R' of IX and to the type of halide in X as well known to the one skilled in the art. For example, for electron-rich aryl- and heteroaryl-halides X, iodo or bromo is preferred over chloro as the halide unless a palladium-catalyst with relatively high activity is employed.

Additional methods for the preparation of intermediates of formula III include standard Knoevenagel condensation between malonic acid XII, and aryl- or heteroaryl aldehydes XIII, followed by decarboxylation (lower part of scheme 3). Furthermore, when aiming for intermediates of formula XI (and then III after hydrolysis, as described above) in which R'≠H, the Heck reaction may be low yielding because of steric hindrance at the terminal position of the double bond of structures such as IX. Instead one may employ the Horner Wadsworth Emmons (HWE) reaction, in which a phosphine oxide of general formula XIV reacts with a heteroaryl ketone of general formula XV (Scheme 4).

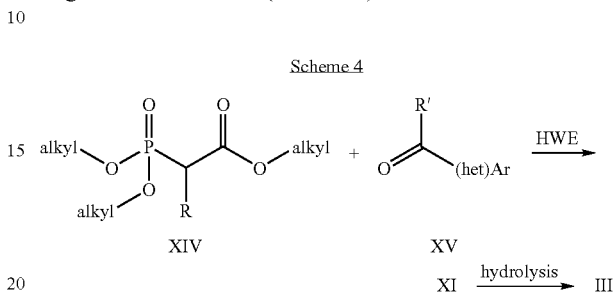

COMPOUND EXAMPLES

General Methods

All materials were obtained from commercial sources, unless not stated otherwise, and were used without further purification unless otherwise noted. DMF was dried over molecular sieves (4 Å). THF was distilled from sodium and benzophenone. HRMS (ESI) spectra were recorded with a micromass Q-TOF Micro spectrometer. NMR spectra (in CDCl3, CD3OD or DMSO-d6) were recorded on a Bruker DRX 400 or on a Bruker Ultrashield 400 spectrometer at 400 MHz. All chemical shifts are in ppm on the delta-scale ($\delta$) relative to TMS using the residual CHCl3 peak in CDCl3, or the residual CD2HOD peak in CD3OD, or the residual CD3SOCD2H peak in (CD3)2SO as internal standard (7.26, 3.31 or 2.50 ppm respectively relative to TMS) and the fine splitting of the signals as appearing in the recordings (s: singlet, d: doublet, t: triplet, q: quartet, m: multiplet, br: broad signal). Flash chromatography was performed using 60 Å 35-70 μm Davisil silica gel. TLC analyses were made on Silica Gel 60 F254 (Merck) plates and visualised under a 254/365 nm UV-lamp.

PREPARATION OF INTERMEDIATES

Below follows non-limiting examples on the synthesis of intermediates useful for the preparation of compounds of formula I.

5,8-Dichloro-6,7-dimethoxy-1,2,3,4-tetrahydroisoquinoline hydrochloride

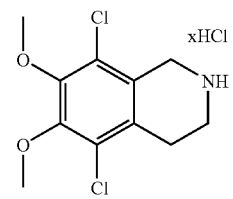

6,7-Dimethoxy-1,2,3,4-tetrahydroisoquinoline hydrochloride (200 mg, 0.870 mmol) was suspended in glacial acetic acid (5 mL) and sulphuryl chloride (154 μL, 1.92 mmol) was added slowly. The resulting mixture was stirred at room temperature for 3 hours and then evaporated to give the title compound (quant) as a yellowish mass.

$^1$H NMR (400 MHz, CD$_3$OD) δ 4.35 (br s, 2H), 3.90 (br d, 6H), 3.50 (br, 2H), 3.05 (br, 2H).

5,8-Dichloro-6,7-dihydroxy-1,2,3,4-tetrahydroisoquinoline hydrobromide

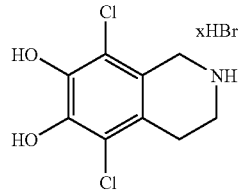

5,8-Dichloro-6,7-dimethoxy-1,2,3,4-tetrahydroisoquinoline hydrochloride (1.0 g, 3.35 mmol) was suspended in aqueous HBr (48%, 10 mL) and refluxed for 5 hours before evaporation. The remaining residue was evaporated twice from toluene to give 1.05 g (quant) of the title compound as a pale solid.

$^1$H NMR (400 MHz, CD$_3$OD) δ 6.60 (s, 1H) 6.57 (s, 1H) 4.26 (s, 2H) 3.50 (t, 2H, J=6 Hz) 3.01 (t, 2H, J=6 Hz).

5,8-Bis(chloromethyl)-6,7-dimethoxy-1,2,3,4-tetrahydroisoquinoline acetamide

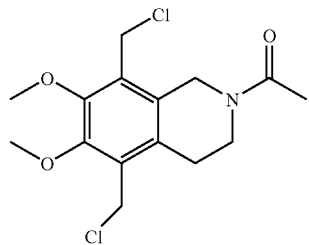

6,7-dimethoxy-1,2,3,4-tetrahydroisoquinoline hydrochloride (2.0 g, 8.71 mmol) was dissolved in water (20 ml) and NaOH (10 ml, 2M aq). The aqueous phase was extracted with dichloromethane (4×20 ml) and the combined organics were dried (MgSO$_4$) and filtered. The filtered liquid was cooled to 0° C. before slow addition of acetyl chloride (620 μl, 8.71 mmol) followed by slow addition of Et$_3$N (1.22 ml, 8.71 mmol). The resulting mixture was stirred at rt for 30 minutes, washed with HCl (2×80 ml, 1M aq.) and NaHCO$_3$ (80 ml, sat aq.), dried (MgSO$_4$), filtered and evaporated into a pale mass.

This mass was dissolved in nitromethane (40 ml) and cooled to 0° C. Tin(IV) chloride (8.15 ml, 70.0 mmol) was added slowly followed by slow addition of methoxyacetyl chloride (3.18 ml, 34.8 mmol) and the resulting mixture was stirred at rt for 24 h. The reaction was then diluted with HCl (30 ml, concentrated. aq.) and extracted with dichloromethane (3×40 ml). Combined organics were washed with water (20 ml), dried (MgSO$_4$), filtered and evaporated into a pale solid foam. The product was purified by flash chromatography using Pet. Ether/EtOAc (1/2) as eluent to give 420 mg (14%) of 5,8-bis(chloromethyl)-6,7-dimethoxy-1,2,3,4-tetrahydroisoquinoline acetamide as a pale, sticky mass.

$^1$H NMR (CDCl$_3$) rot. mix. δ 4.77-4.55 (br, 2H) 4.20-4.05 (br, 2H) 3.82 (s, 6H) 4.81-4.70 (br, 2H) 3.96-3.85 (br, 2H) 3.85-3.75 (br, 1H) 3.75-3.63 (br, 2H) 2.94-2.83 (br, 2H) 2.80-2.62 (br, 2H) 1.46 (s, 9H). TLC (Pet. Ether/EtOAc 1/1) R$_f$ 0.23.

6,7-Dimethoxy-5,8-dimethyl-1,2,3,4-tetrahydroisoquinoline acetamide

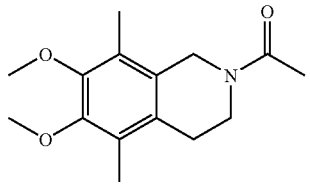

5,8-Bis(chloromethyl)-6,7-dimethoxy-1,2,3,4-dihydroisoquinoline acetamide (420 mg, 1.26 mmol), was dissolved in DMF (6 ml) at rt. Sodium cyanoborohydride (199 mg, 3.16 mmol) was added and the reaction was stirred at 100° C. for 20 h. The reaction was cooled, diluted with HCl (60 ml, 1M aq.) and extracted with EtOAc (3×20 ml). Combined organics were washed with NaHCO$_3$ (30 ml, sat. aq.) followed by brine (30 ml), dried (MgSO$_4$), filtered and evaporated to give 396 mg of crude 6,7-dimethoxy-5,8-dimethyl-1,2,3,4-tetrahydroisoquinoline acetamide as a pale oil. This material was used in subsequent reactions without further purification.

$^1$H NMR (CDCl$_3$) rot. mix. δ 4.55 (ma) (s, 2H) 4.43 (mi) (s, 2H) 3.79 (mi) (br t, 2H) 3.78 (s, 6H) 3.65 (ma) (br t, 2H) 2.73 (ma) (br t, 2H) 2.66 (mi) (br t, 2H) 2.18 (br d, 3H) 2.13 (br d, 3H) 2.02 (s, 3H).

6,7-Dimethoxy-5,8-dimethyl-1,2,3,4-tetrahydroisoquinoline

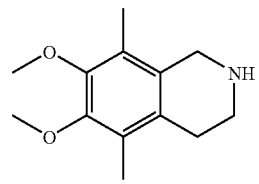

6,7-Dimethoxy-5,8-dimethyl-1,2,3,4-tetrahydroisoquinoline acetamide (396 mg) was dissolved in 1,4-dioxane (10 ml). NaOH (10 ml, 2M aq.) was added and the mixture was refluxed for 21 h. Organic solvents were evaporated and the aq. residue was extracted with dichloromethane (4×20 ml). Combined organics were dried (MgSO$_4$), filtered and evaporated. The product was purified by flash chromatography using EtOAc/MeOH/Et$_3$N (20/2/1→16/4/1) as eluent to give 116 mg (42%) of 6,7-dimethoxy-5,8-dimethyl-1,2,3,4-tetrahydroisoquinoline as a clear, oily residue.

$^1$H NMR (CDCl$_3$) δ 3.87 (s, 2H) 3.80 (s, 6H) 3.13 (t, J=6 Hz, 2H) 2.60 (t, J=6 Hz, 2H) 2.14 (s, 3H) 2.09 (s, 3H).

TLC (EtOAc/MeOH/Et$_3$N 16/4/1) R$_f$ 0.35.

3-Iodo-2-(piperidin-1-yl)-6-(trifluoromethyl)pyridine

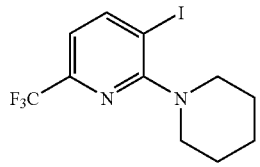

A solution of 2-chloro-3-iodo-6-(trifluoromethyl)pyridine (Tet. Lett., 1998, 39(13), 1749-1752) (350 mg, 1.14 mmol), piperidine (135 μl, 1.37 mmol) and Et$_3$N (640 μl, 4.56 mmol) in i-PrOH (2 mL) was heated for 1 h at 140° C. in a microwave reactor. The reaction mixture was concentrated to dryness and the crude was purified through flash chromatography (SiO$_2$, heptane) to afford 237 mg (58%) of the title compound.

$^1$H NMR (CDCl$_3$) δ 8.17 (dd, J=7.6 Hz, J=0.8 Hz, 1H) 6.91 (d, J=7.6 Hz, 1H) 3.29 (m, 4H) 1.75 (m, 4H) 1.63 (m, 2H).

General Procedure for the Heck Reaction to Yield Compounds X (Scheme 3)

Aryl bromide X (1.0 equiv.), Pd(OAc)$_2$ (2 mol %), DABCO (4 mol %) and K$_2$CO$_3$ (1.0 equiv.) were suspended in DMF (5.2 mL/mmol aryl bromide X) together with the unsaturated ester IX (1.5 equiv.). The mixture was flushed with argon before the tube was sealed and heated at 125° C. for 12 hours. Then, the mixture was filtered through Celite, rinsed with CH$_2$Cl$_2$ and evaporated. The remaining residue was then purified by column chromatography to yield compounds XI.

The following compounds were prepared according to the general procedure described above.

(E)-Methyl 3-(quinolin-3-yl)acrylate

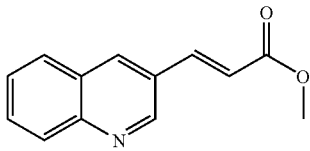

The title compound was obtained as a white solid in 85% yield (SiO$_2$, petroleum ether/ethyl acetate 85/15→50/50).

$^1$H NMR (400 MHz, CDCl$_3$) δ 9.10 (d, 1H, J=2.0 Hz) 8.25 (d, 1H, J=2.0 Hz) 8.12 (d, 1H, J=8.4 Hz) 7.86 (d, 1H, J=16.0 Hz) 7.87-7.85 (m, 1H) 7.78-7.74 (m, 1H) 7.62-7.58 (m, 1H) 6.68 (d, 1H, J=16.0 Hz) 3.86 (s, 3H).

(E/Z)-Methyl 3-(quinolin-3-yl)but-2-enoate

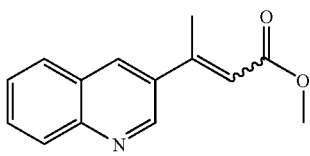

The title compound was obtained as a diastereomeric mixture (E- and Z-isomers), as a white solid, in 52% yield. R$_f$ 0.21 (SiO$_2$, petroleum ether/ethyl acetate 80/20).

$^1$H NMR (400 MHz, CDCl$_3$) δ 9.05 (d, 1H, J=2.4 Hz) 8.22 (d, 1H, J=2.4 Hz) 8.13-8.11 (m, 1H) 7.87-7.85 (m, 1H) 7.77-7.73 (m, 1H) 7.61-7.57 (m, 1H) 6.34-6.33 (m, 1H) 3.81 (s, 3H) 2.71 (s, 3H).

(E)-ethyl 3-(6-(trifluoromethyl)pyridin-3-yl)acrylate

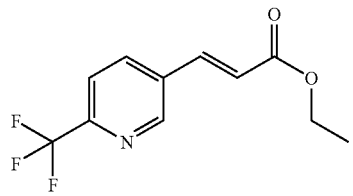

This material was used directly in the next step without any further purification.

Yield: 97%.

$^1$H NMR (CDCl$_3$) δ 8.85 (d, J=1.6 Hz, 1H) 8.00 (dd, J=2.0, 8.0 Hz, 1H) 7.72 (d, J=8.4 Hz, 1H) 7.71 (d, J=16.0 Hz, 1H) 6.60 (d, J=16.0 Hz, 1H) 4.31 (q, J=7.2 Hz, 2H) 1.36 (t, J=7.2 Hz, 3H).

(E)-methyl 3-(2-(piperidin-1-yl)-6-(trifluoromethyl)pyridin-3-yl)acrylate

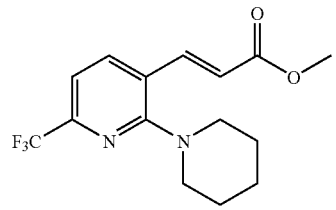

70 μl (1.0 mmol) methyl acrylate was added to a mixture of 237 mg (0.66 mmol) 3-iodo-2-(piperidin-1-yl)-6-(trifluoromethyl)pyridine, 3 mg (0.01 mmol) Pd(OAc)$_2$, 2.2 mg (0.02 mmol) DABCO and 91 mg (0.66 mmol) K$_2$CO$_3$ in 3 ml DMF under a nitrogen atmosphere. The reaction mixture was stirred in a sealed tube at 80° C. for 24 h. The mixture was cooled to RT, filtered through celite with EtOAc eluation. The organic phase was washed with water, dried and concentrated. Flash chromatography (SiO$_2$, Pet. Ether/EtOAc 8/1) afforded 196 mg (94%) of the title compound.

$^1$H NMR (CDCl$_3$) δ 7.74 (d, 1H), 7.69 (d, 1H), 7.15 (d, 1H), 6.42 (d, 1H), 3.82 (s, 3H), 3.28 (m, 4H), 1.72 (m, 4H), 1.65 (m, 2H).

1-(6-(Trifluoromethyl)pyridin-3-yl)ethanone

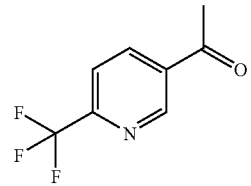

To a solution of 2-trifluoromethyl-5-bromopyridine (5.0 g, 22 mmol) in Et$_2$O (50 mL) was added sec-BuLi (0.91 M in cyclohexane, 24 mL, 22 mmol) at −78° C. After 10 minutes of stirring, N,N-dimethylaminoacetamide (2.3 mL, 24 mmol) dissolved in Et$_2$O (10 mL) was added drop wise. Stirring was continued at −78° C. for 1 h and then at rt over night. The reaction mixture was poured into water (100 mL) and the water phase was extracted with Et$_2$O (3×100 mL). Combined organics were washed with water and brine and dried (MgSO$_4$). After careful evaporation of the solvent, the crude was purified by column chromotography (SiO$_2$, pentane/ether 9/1) to give the title compound (2.3 g, 12 mmol, 54%) as a light yellow solid.

$^1$H NMR (CDCl$_3$) δ 9.26 (br s, 1H) 8.43 (br d, J=5.6 Hz, 1H) 7.83 (br d, J=7.2 Hz, 1H) 2.71 (s, 3H).

Ethyl 3-(6-(trifluoromethyl)pyridin-3-yl)but-2-enoate

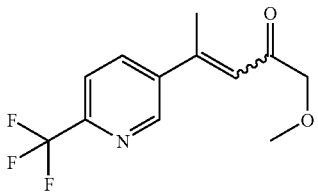

Triethyl phosphonoacetate (6.2 mL, 31 mmol) was added drop wise to a suspension of NaH (95%, 760 mg, 30 mmol) in dry THF (10 mL) at 0° C. After 30 minutes of stirring at 0° C., 1-(6-(trifluoromethyl)pyridin-3-yl)ethanone (2.3 g, 12 mmol) in THF (8 mL) was added drop wise. The resulting mixture was heated at reflux for 12 h and was then allowed to cool to rt. The reaction mixture was poured into sat. NH$_4$Cl (aq.) (15 mL) and extracted with Et$_2$O (3×15 mL). Combined organics were washed with water and brine and dried (MgSO$_4$). After evaporation the crude was purified by column chromatography (SiO$_2$, Pet. Ether/EtOAc 95/5) to give the title compound (2.9 g, 11 mmol, 94%) as a light yellow oil, as a mixture of E- and Z-isomers.

$^1$H NMR (CDCl$_3$) δ 8.81 (br s, 1H) 7.92 (br d, J=8.4 Hz, 1H) 7.71 (br d, J=8.0 Hz, 1H) 6.19 (br s, 1H) 4.26 (q, J=7.2 Hz, 2H) 2.60 (br s, 3H) 1.34 (t, J=7.2 Hz, 3H).

1-(5-Fluoropyridin-2-yl)ethanone

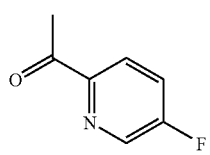

sec-BuLi (1.9 mL, 1.4 M in hexane) was added drop wise to a solution of 2-bromo-5-fluoropyridine (500 mg, 2.8 mmol) in dry Et$_2$O (6 mL) at −78° C. Stirring was continued at this temperature for 10 minutes, after which a solution of N,N-dimethylacetamide (290 μL, 3.1 mmol) in dry Et$_2$O (1 mL) was added drop wise. Stirring was continued at −78° C. for 1 h, where after the reaction mixture was allowed to slowly reach rt. The reaction mixture was again cooled to −78° C. and was quenched by adding 1M HCl aq. solution (6 mL) before it was left to warm to rt over night. The water and organic phases were separated and the water phase extracted with Et$_2$O (2×10 mL). Combined organics were washed with water and brine and dried (MgSO$_4$). After filtration and Careful! evaporation (the title compound is volatile) the red/brown oily crude was dissolved in CH$_2$Cl$_2$ and a small amount of SiO$_2$ was added. The suspension was filtered through a pad of Celite and the solvent was removed by evaporation to give the title compound (203 mg, 1.5 mmol, 52%) as an orange oil. The product was considered to be pure enough to be used directly in the next step without prior purification.

$^1$H NMR (CD$_3$OD) δ 8.51 (d, J=2.8 Hz, 1H) 8.11 (ddd, J=0.4, 4.8, 8.8 Hz, 1H) 7.52 (ddt, 0.8, 2.8, 8.8 Hz, 1H) 2.71 (s, 3H).

General Procedure for Ester Hydrolysis (Scheme 3)

A solution of NaOH (s) (500 mg) in water (1.1 mL) was added to a methanolic solution of the ester XI (2.5 mmol). Stirring was continued at rt for 2 h. After that, the reaction mixture was neutralized by adding 1M HCl (aq.). A white precipitate formed which was isolated by filtration and washed with water and methanol. The white crystalline product was dried in a vacuum oven at 45° C.

The following compounds were prepared according to the general procedure described above.

(E)-3-(quinolin-3-yl)acrylic acid

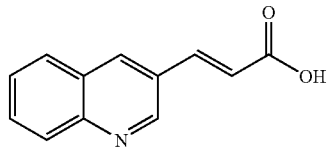

The title compound was obtained as a white solid in 71% yield and was used directly in the next step without further purification.

(E)-3-(quinolin-3-yl)but-2-enoic acid

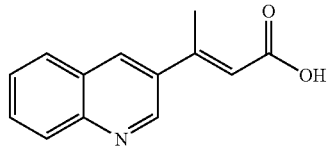

The title compound was obtained as a white solid in 94% yield and was used directly in the next step without further purification.

The following compounds of formula III were also prepared as indicated (E)-3-(6-(trifluoromethyl)pyridin-3-yl)acrylic acid

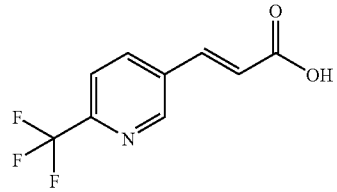

To a solution of (E)-ethyl-3-(6-(trifluoromethyl)pyridin-3-yl)acrylate (2.65 g, 10.8 mmol) in THF/EtOH (1/1, 20 mL) was added 2.28 M NaOH (aq.) (14.2 mL) at rt. The reaction mixture was stirred at rt for 4 h and was then neutralized by adding 1M HCl(aq.). The water-phase was extracted with CH₂Cl₂/MeOH 9/1 (5×20 mL), the combined organics dried (MgSO₄), filtered and evaporated to give the title compound (2.15 g, 9.90 mmol, 91%) as an off white solid. This material was used directly in the next step without further purification.

$^1$H NMR (CD$_3$OD) δ 8.91 (d, J=1.6 Hz, 1H) 8.29 (dd, J=2.0, 8.4 Hz, 1H) 7.85 (d, J=8.4 Hz, 1H) 7.75 (d, J=16.0 Hz, 1H) 6.75 8d, J=16.0 Hz, 1H).

3-(6-(Trifluoromethyl)pyridin-3-yl)but-2-enoic acid

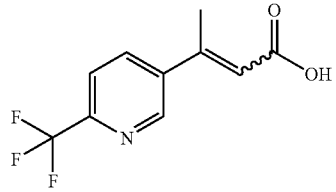

To a solution of ethyl 3-(6-(trifluoromethyl)pyridin-3-yl)but-2-enoate (2.9 g, 11 mmol) in EtOH/THF 1/1 (34 mL) was added 1M NaOH (aq.) (34 mL). The resulting mixture was heated at 60° C. for 1 h after which the reaction mixture was allowed to cool to rt. The volatiles were evaporated and the remaining water phase neutralized with 1 M HCl(aq.). The title compound (2.4 g, 10 mmol, 91%), which precipitated as a white solid, was filtered off and dried under vacuum at 55° C. over night. This material was used directly in the next step, without further purification.

(E)-3-(2-methyl-6-(trifluoromethyl)pyridin-3-yl) acrylic acid

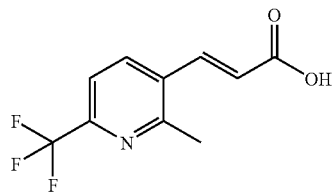

To a solution of (E)-methyl 3-(2-methyl-6-(trifluoromethyl)pyridin-3-yl)acrylate (Gray, M.; Andrews, I. P.; Hook, D. F.; Kitteringham, J.; Voyle, M. *Tet. Lett.* 2001, 41, 6237-6240.) (150 mg, 0.61 mmol) in MeOH (2.0 mL) was added 1M NaOH (aq.) (1.8 mL). The reaction mixture was stirred for 2 h at 40° C. The volatiles were then evaporated and the remaining water phase neutralized with 1M HCl (aq). The title compound (141 mg, 0.61 mmol, quant.), which precipitated as a white solid, was filtered off and dried under vacuum at 45° C. This material was used directly in the next step without further purification.

(E,Z)-3-(5-fluoropyridin-2-yl)but-2-enoic acid

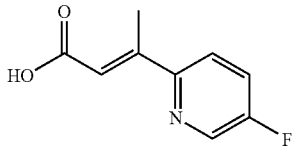

Triethyl phosphonoacetate (740 μL, 3.7 mmol) was added drop wise to a suspension of NaH (95%, 86 mg, 3.6 mmol) in dry THF (1.0 mL) at 0° C. Stirring was continued at this temperature for 30 minutes, after which a solution of 1-(5-fluoropyridin-2-yl)ethanone (200 mg, 1.4 mmol) in dry THF (1 mL) was added drop wise to the reaction mixture. The resulting mixture was heated at reflux for 6 h and was then left to cool to rt over night. The reaction was quenched by careful addition of NH₄Cl sat. aq. solution (1.5 mL) and was then extracted with Et₂O (2×10 mL). Combined organics were washed with water and brine and dried (MgSO₄). After filtration and evaporation crude (E,Z)-ethyl 3-(5-fluoropyridin-2-yl)but-2-enoate was obtained pure enough to be used directly in the next step.

1M NaOH aq. solution (4.2 mL) was added to a solution of (E,Z)-ethyl 3-(5-fluoropyridin-2-yl)but-2-enoate (293 mg, 1.4 mmol) in EtOH/THF (4 mL, 1/1). The resulting mixture was heated at 40° C. for 12 h and was then left to cool to rt. The volatiles were evaporated and the remaining water phase acidified to pH 6-7 using 1 M HCl aq. solution. The water phase was extracted with CH₂Cl₂ (5×10 mL) and combined organics were washed with brine and dried (MgSO₄). After filtration and evaporation the title compound (190 mg, 1.0 mmol, 75%) was obtained as a mixture of E- and Z-isomers which was considered to be pure enough to be used directly in the next step. The isomers were not separated at this stage.

$^1$H NMR (CD$_3$OD) δ 8.48 (d, J=3.2 Hz, 1H) 7.78-7.73 (m, 1H) 7.66-7.60 (m, 1H) 6.63 (d, J=1.2 Hz, 1H) 2.56 (d, J=1.6 Hz, 3H).

General Procedure for Amide Coupling to Yield Methyl Ethers of Formula I (R1=R2=methyl, Scheme 1)

5,8-dichloro-6,7-dimethoxy-1,2,3,4-tetrahydroisoquinoline hydrochloride (1.0 mmol), a carboxylic acid of general formula III (1.1 mmol), EDC.HCl (1.5 mmol), HOBt (1.0 mmol), DMAP (2.0 mmol) and cesium carbonate (2.0 mmol) were suspended in DMF (30 mL) and stirred at rt for 48 h. The reaction mixture was then diluted with water (30 mL) and extracted with EtOAc (3×30 mL). The combined organics were washed with NaHCO₃ (2×30 mL, sat aq), water (3×30 mL) and brine and dried (MgSO₄). After evaporation the resulting methyl ethers of formula I were purified by column chromatography.

The following compounds were prepared according to the general procedure described above.

(E)-1-(5,8-dichloro-6,7-dimethoxy-3,4-dihydroisoquinolin-2(1H)-yl)-3-(pyridin-3-yl)prop-2-en-1-one

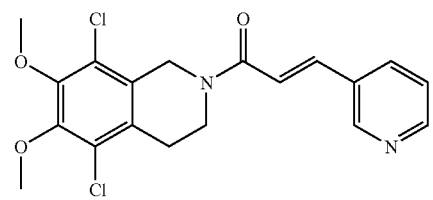

The title compound was obtained as a yellowish oil in 52% yield, $R_f$ 0.26 (SiO$_2$, petroleum ether/ethyl acetate 3/7).

$^1$H NMR (400 MHz, CDCl$_3$) rot. mix. δ 8.79 (d, 1H, J=2.0 Hz) 8.59 (dd, 1H, J=1.6, 4.8 Hz) 7.85 (td, 1H, J=1.8, 8.0 Hz) 7.71 (d, 1H, J=15.6 Hz) 7.35-7.32 (m, 1H) 7.04 (d, 1H, J=15.6 Hz) 4.82-4.75 (ma+mi, m, 2H) 3.99-3.84 (m, 2H) 3.91 (br s, 6H) 2.99-2.88 (m, 2H).

(E)-1-(5,8-dichloro-6,7-dimethoxy-3,4-dihydroisoquinolin-2-(1H)-yl)-3-(5-fluoropyridin-2-yl)prop-2-en-1-one

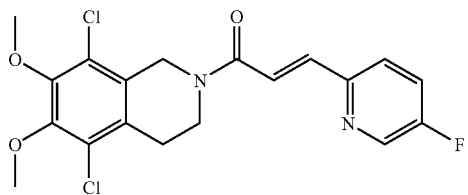

The title compound was obtained as a colourless oil in 47% yield, $R_f$ 0.28 (SiO$_2$, petroleum ether/ethyl acetate 1/1).

$^1$H NMR (400 MHz, MeOD) rot. mix. δ 8.53 (d, 1H, J=2.8 Hz) 7.74-7.62 (m, 4H) 4.82 (br s, 2H) 4.01-3.98 (m, 2H) 3.89 (br s, 6H) 2.99-2.90 (ma+mi, m, 2H).

(E)-1-(5,8-dichloro-6,7-dimethoxy-3,4-dihydroisoquinolin-2(1H)-yl)-3-(quinolin-3-yl)prop-2-en-1-one

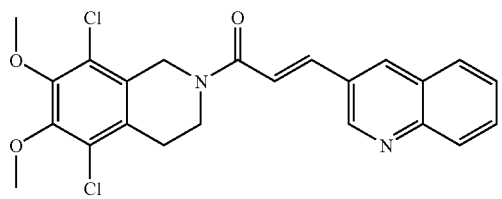

The title compound was obtained as a white solid in 39% yield (SiO$_2$, petroleum ether/ethyl acetate).

$^1$H NMR (400 MHz, CDCl$_3$) rot. mix. δ 9.15 (d, 1H, J=2.4 Hz) 8.26 (d, 1H, J=2.0 Hz) 8.13 (d, 1H, J=8.4 Hz) 7.90 (d, 1H, J=15.6 Hz) 7.88 (br d, 1H, J=7.2 Hz) 7.78-7.74 (m, 1H) 7.62-7.58 (m, 1H) 7.21 (d, 1H, J=15.2 Hz) 4.87-4.82 (ma+mi) (m, 2H) 3.99-3.91 (m, 2H) 3.93 (s, 3H) 3.92 (s, 3H) 3.00-2.94 (ma+mi, m, 2H).

(E)-1-(5,8-dichloro-6,7-dimethoxy-3,4-dihydroisoquinolin-2(1H)-yl)-3-(quinolin-3-yl)but-2-en-1-one

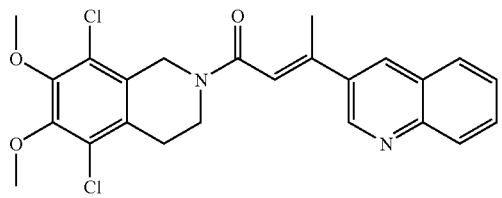

The title compound was obtained as a colourless oil in 40% yield (SiO$_2$, petroleum ether/ethyl acetate 6/4).

$^1$H NMR (400 MHz, CDCl$_3$) rot. mix. δ 9.10 (d, 1H, J=2.0 Hz) 8.20 (br s, 1H) 8.13 (br d, 1H, J=8.4 Hz) 7.87 (br d, 1H, J=8.0 Hz) 7.75 (br t, 1H, J=7.8 Hz) 7.60 (br t, 1H, J=7.4 Hz) 6.57 (br s, 1H) 4.84 (ma, br s, 2H) 4.71 (m, br s, 2H) 3.98-3.81 (ma+mi, m, 2H) 3.93 (s, 6H) 2.97-2.89 (m, 2H) 2.45 (ma, br s, 2H) 2.41 (m, br s, 2H).

(E)-1-(5,8-dichloro-6,7-dimethoxy-3,4-dihydroisoquinolin-2(1H)-yl)-3-(4-methoxyphenyl)prop-2-en-1-one

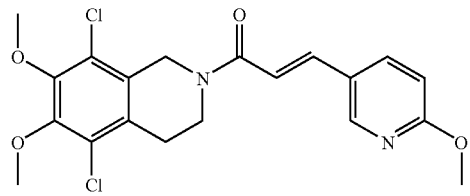

The title compound was obtained as a white solid in 43% yield (SiO$_2$, petroleum ether/ethyl acetate 75/25).

$^1$H NMR (400 MHz, DMSO-d$_6$) rot. mix. δ 7.76-7.64 (m, 2H) 7.50 (br d, 1H, J=15.2 Hz) 7.23 (br d, 1H, J=15.2 Hz) 6.99-6.96 (m, 2H) 4.78 (m, br s, 2H) 4.70 (ma, br s, 2H) 4.02-3.91 (m, 2H) 3.84 (s, 3H) 3.83 (s, 3H) 3.80 (s, 3H) 2.87-2.72 (m, 2H).

(Z)-1-(5,8-dichloro-6,7-dimethoxy-3,4-dihydroisoquinolin-2(1H)-yl)-3-(2-methoxyphenyl)prop-2-en-1-one

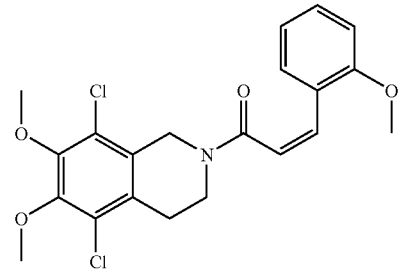

The title compound was obtained as a colourless oil in 46% yield, (SiO$_2$, petroleum ether/ethyl acetate 8/2).

$^1$H NMR (400 MHz, MeOD) rot. mix. δ 7.06-7.00 (m, 2H) 7.00 (d, 1H, J=12.4 Hz) 6.95-6.91 (m, 1H) 6.63-6.61 (m, 1H) 6.56-6.52 (m, 1H) 6.08 (d, 1H, J=12.4 Hz) 4.66 (m, br s, 2H) 4.39 (ma, br s, 2H) 3.86 (s, 3H) 3.83 (s, 3H) 3.79 (ma, t, 2H, J=6.0 Hz) 3.76 (s, 3H) 3.61 (m, t, 2H, J=6.0 Hz) 2.66 (ma, t, 2H, J=6.0 Hz) 2.35 (m, t, 2H, J=6.0 Hz).

(E)-1-(5,8-dichloro-6,7-dimethoxy-3,4-dihydroisoquinolin-2(1H)-yl)-3-(5-fluoropyridin-2-yl)but-2-en-1-one

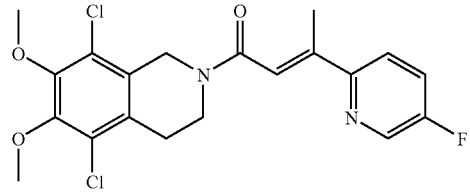

The title compound was obtained as a yellow solid in 32% yield (SiO$_2$, Pet. ether/EtOAc 75/25). The Z-isomer was not isolated.

$^1$H NMR (CDCl$_3$) rot. mix. δ 8.47 (d, J=2.8 Hz, 1H) 7.54-7.50 (m, 1H) 7.45-7.39 (m, 1H) 7.05 (ma) (s, 1H) 7.00 (mi) (s, 1H) 4.82 (ma) (s, 2H) 4.66 (mi) (s, 2H) 3.91 (s, 6H) 3.86-3.76 (m, 2H) 2.94-2.86 (m, 2H) 2.33 (br s, 3H).

The following methyl ether of formula I (Scheme 1, R1-R4=methyl) was also prepared as indicated.

(E)-6,7-dimethoxy-5,8-dimethyl-1,2,3,4-tetrahydroisoquinoline 3-(6-(trifluoromethyl)pyridin-3-yl)acrylamide

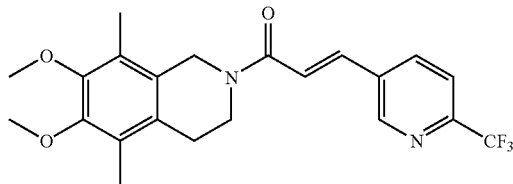

6,7-dimethoxy-5,8-dimethyl-1,2,3,4-tetrahydroisoquinoline (116 mg, 0.52 mmol), (E)-3-(6-(trifluoromethyl)pyridin-3-yl)acrylic acid (114 mg, 0.52 mg), PyBroP (269 mg, 0.58 mmol) and DMAP (128 mg, 1.05 mmol) were suspended in THF (12 ml) and stirred at rt for 2.5 h before evaporation. The product was purified by flash chromatography using Pet. Ether/EtOAc (2/1→1/1) as eluent to give 190 mg (87%) of (E)-6,7-dimethoxy-5,8-dimethyl-1,2,3,4-tetrahydroisoquinoline 3-(6-(trifluoromethyl)pyridin-3-yl)acrylamide as a pale solid.

$^1$H NMR (CDCl$_3$) rot. mix. δ 8.87 (s, 1H) 8.00 (br d, 1H) 7.72 (br d, 1H) 7.70 (d, J=8 Hz, 1H) 7.14 (d, J=16 Hz) 4.71 (ma) (br s, 2H) 4.64 (mi) (br s, 2H) 3.93 (mi) (br, 2H) 3.88 (ma) (br, 2H) 3.81 (s, 6H) 2.82 (ma) (br, 2H) 2.76 (mi) (br, 2H) 2.18 (s, 3H) 2.16 (s, 3H). TLC (Pet. Ether/EtOAc 1/1) R$_f$ 0.66.

PREPARATION OF FINAL COMPOUNDS

The following non-limiting examples of compounds of formula I did all show less than 80% remaining contraction, at a concentration of 100$\mu$, of human bronchiols after LTD4 induced contraction according to the method described herein.

Example 1

(E)-1-(5,8-dichloro-6,7-dihydroxy-3,4-dihydroisoquinolin-2(1H)-yl)-3-phenylprop-2-en-1-one

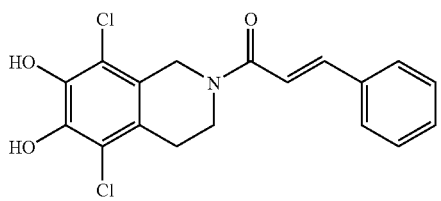

trans-Cinnamoyl chloride (79 mg, 0.476 mmol) was suspended in DMF (7 mL) together with 5,8-dichloro-6,7-dihydroxy-1,2,3,4-tetrahydroisoquinoline hydrobromide (150 mg, 0.476 mmol) followed by triethylamine (133 µL, 0.952 mmol). The resulting mixture was stirred at room temperature for 16 hours and then diluted with ethyl acetate (50 mL). The resulting mixture was washed twice with saturated sodium bicarbonate (2×40 mL), dried (MgSO$_4$) and evaporated into a yellowish mass. Purification with column chromatography (petroleum ether/ethyl acetate 1/1→1/2) yielded 69 mg (40%) of the title compound as a yellowish solid.

$^1$H NMR (400 MHz, CD$_3$OD) rot. mix. δ 7.70-7.56 (m, 3H) 7.44-7.33 (m, 3H) 7.21 (br d, 1H) 4.78 (m, s, 2H) 4.71 (ma, s, 2H) 4.00-3.93 (ma, br t, 2H) 3.92-3.86 (m, br t, 2H) 2.92-2.86 (ma, br t, 2H) 2.85-2.69 (m, br t, 2H).

TLC (petroleum ether/ethyl acetate 1/1) R$_f$ 0.33.

HRMS (ESI) calc for C$_{18}$H$_{16}$NO$_3$Cl$_2$ [M+H] 364.0507, found 364.0539.

General Procedure for the Demethylation of Methyl Ethers of Formula I

A methyl ether of formula I (R1,R2=Me) (1.0 equiv.) was dissolved in CH$_2$Cl$_2$ (20 mL) and cooled to 0° C. Boron tribromide (1M in CH$_2$Cl$_2$, 3.0 equiv.) was then added slowly and the resulting mixture was stirred at 0° C. for 5 minutes, then at rt for 12 h. The reactions were quenched with methanol (5 mL) and evaporated to dryness. The obtained residue was dissolved in methanol (20 mL), sodium bicarbonate (6.16 mmol) was added and the resulting suspension was stirred at rt for 30 minutes before evaporation. The resulting crude products were then purified by column chromatography.

Example 2

(E)-1-(5,8-dichloro-6,7-dihydroxy-3,4-dihydroisoquinolin-2(1H)-yl)-3-(pyridin-3-yl)prop-2-en-1-one

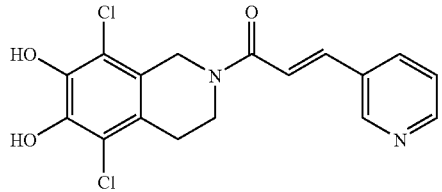

The title compound was obtained from (E)-1-(5,8-dichloro-6,7-dimethoxy-3,4-dihydroisoquinolin-2(1H)-yl)-3-(pyridin-3-yl)prop-2-en-1-one as an orange solid in 19% yield, R$_f$ 0.08 (SiO$_2$, ethyl acetate).

$^1$H NMR (400 MHz, DMSO-d$_6$) rot. mix. δ 9.59 (br s, 1H(OH)) 8.91 (br s, 1H) 8.56 (dd, 1H, J=1.6, 4.8 Hz) 8.23 (br d, 1H, J=8.0 Hz) 7.59-7.43 (m, 3H) 4.74 (m, br s, 2H) 4.63 (ma, br s, 2H) 3.97-3.94 (ma, m, 2H) 3.83-3.76 (m, m, 2H) 2.83-2.73 (ma, m, 2H) 2.73-2.65 (m, m, 2H).

HRMS (ESI) calc for C$_{17}$H$_{15}$Cl$_2$N$_2$O$_3$ [M+H] 365.0460, found 365.0425.

Example 3

(E)-1-(5,8-dichloro-6,7-dihydroxy-3,4-dihydroisoquinolin-2-(1H)-yl)-3-(5-fluoropyridin-2-yl)prop-2-en-1-one

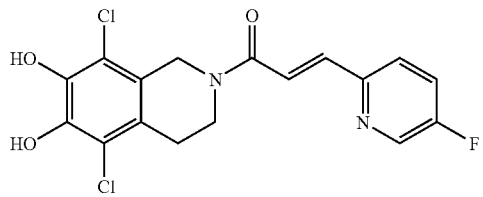

The title compound was obtained from (E)-1-(5,8-dichloro-6,7-dimethoxy-3,4-dihydroisoquinolin-2-(1H)-yl)-3-(5-fluoropyridin-2-yl)prop-2-en-1-one as a yellow solid in 86% yield, $R_f$ 0.13 (SiO$_2$, chloroform/methanol 9/1).

$^1$H NMR (400 MHz, DMSO-d$_6$) rot. mix. δ 9.60 (s, 1H) 9.57 (s, 1H(OH)) 8.63 (s, 1H) 7.94-7.90 (m, 1H) 7.83-7.80 (m, 1H) 7.56 (s, 2H) 4.70 (m, br s, 2H) 4.63 (ma, br s, 2H) 3.90-3.80 (ma+mi, m, 2H) 2.78-2.67 (ma+mi, m, 2H).

HRMS (ESI) calc for C$_{17}$H$_{13}$Cl$_2$FN$_2$O$_3$ [M+H] 383.0366, found 383.0354.

Example 4

(E)-1-(5,8-dichloro-6,7-dihydroxy-3,4-dihydroisoquinolin-2(1H)-yl)-3-(quinolin-3-yl)prop-2-en-1-one

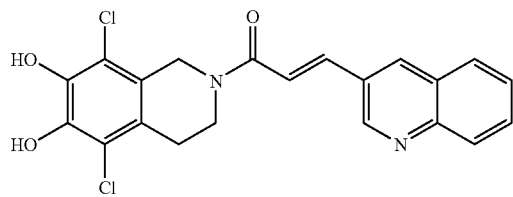

The crude title compound was obtained from (E)-1-(5,8-dichloro-6,7-dimethoxy-3,4-dihydroisoquinolin-2(1H)-yl)-3-(quinolin-3-yl)prop-2-en-1-one, and was purified via the following procedure: The crude was dissolved in methanol. After addition of a small amount of SiO$_2$ the mixture was filtered through Celite and the solvent evaporated. The oily residue was dissolved in a small amount of methanol and the product precipitated via addition of petroleum ether. The solvent was decanted. The title compound was obtained as a greenish solid in 61% yield.

$^1$H NMR (400 MHz, MeOD) rot. mix. δ 9.60 (br d, 1H, J=9.2 Hz) 9.40 (br s, 1H) 8.35 (br d, 1H, J=8.4 Hz) 8.23 (br d, 1H, J=8.4 Hz) 8.17 (br t, 1H, J=7.6 Hz) 7.99 (br t, 1H, J=7.6 Hz) 7.90-7.71 (m, 2H) 4.79 (br s, 2H) 4.09-4.03 (ma, m, 2H) 3.98-3.92 (m, m, 2H) 3.00-2.92 (ma, m, 2H) 2.89-2.81 (m, m, 2H). HRMS (ESI) calc for C$_{21}$H$_{17}$Cl$_2$N$_2$O$_3$ [M+H] 415.0616, found 415.0598.

Example 5

(E)-1-(5,8-dichloro-6,7-dihydroxy-3,4-dihydroisoquinolin-2(1H)-yl)-3-(quinolin-3-yl)but-2-en-1-one

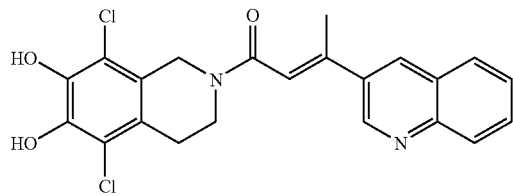

The title compound was obtained from (E)-1-(5,8-dichloro-6,7-dimethoxy-3,4-dihydroisoquinolin-2(1H)-yl)-3-(quinolin-3-yl)but-2-en-1-one as a yellow solid in 14% yield (SiO$_2$, ethyl acetate/methanol 95/5).

$^1$H NMR (400 MHz,) rot. mix. δ 9.62-9.57 (m, 1H) 9.23-9.18 (m, 1H) 8.54-8.49 (m, 1H) 8.06-8.01 (m, 2H) 7.80-7.76 (m, 1H) 7.66-7.63 (m, 1H) 6.91 (s, 1H) 4.63 (br s, 2H) 3.82-3.79 (m, 2H) 2.79-2.73 (ma+mi, m, 2H) 2.33 (ma, br s, 3H) 2.23 (m, br s, 3H).

HRMS (ESI) calc for C$_{22}$H$_{19}$Cl$_2$N$_2$O$_3$ [M+H] 429.0773, found 429.0836.

Example 6

(E)-1-(5,8-dichloro-6,7-dihydroxy-3,4-dihydroisoquinolin-2(1H)-yl)-3-(4-hydroxyphenyl)prop-2-en-1-one

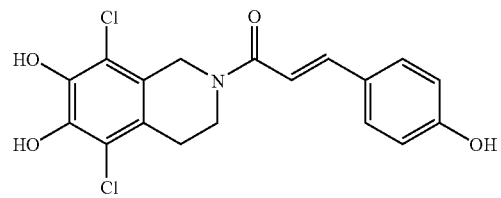

The title compound was obtained from (E)-1-(5,8-dichloro-6,7-dimethoxy-3,4-dihydroisoquinolin-2(1H)-yl)-3-(4-methoxyphenyl)prop-2-en-1-one as an orange solid in 97% yield, $R_f$ 0.34 (SiO$_2$, petroleum ether/ethyl acetate 1/1+ 15% EtOH).

$^1$H NMR (400 MHz, MeOD) rot. mix. δ 7.60-7.51 (m, 3H) 7.07-6.95 (m, 1H) 6.82-6.80 (m, 2H) 4.80-4.69 (mi+ma) (m, 2H) 4.00-3.84 (ma+mi, m, 2H) 2.94-2.77 (ma+mi, m, 2H).

HRMS (ESI) calc for C$_{18}$H$_{16}$Cl$_2$NO$_4$ [M+H] 380.0456, found 380.0393.

Example 7

(Z)-1-(5,8-dichloro-6,7-dihyroxy-3,4-dihydroisoquinolin-2(1H)-yl)-3-(2-hydroxyphenyl)prop-2-en-1-one

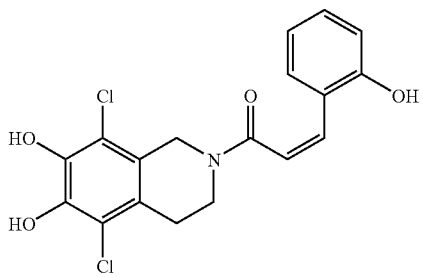

The title compound was obtained from (Z)-1-(5,8-dichloro-6,7-dimethoxy-3,4-dihydroisoquinolin-2(1H)-yl)-3-(2-methoxyphenyl)prop-2-en-1-one as a yellow solid in 29% yield, $R_f$ 0.38 (SiO$_2$, petroleum ether/ethyl acetate 1/1+ 5% EtOH).

$^1$H NMR (400 MHz, MeOD) rot. mix. δ 7.96-7.83 (m, 1H) 7.61-7.47 (m, 1H) 7.38-7.27 (m, 1H) 7.22-7.17 (m, 1H) 6.88-6.84 (m, 2H) 4.78-4.75 (mi+ma) (m, 2H) 4.00-3.87 (m, 2H) 2.97-2.79 (ma+mi, m, 2H).

HRMS (ESI) calc for C$_{18}$H$_{16}$Cl$_2$NO$_4$ [M+H] 380.0456, found 380.0422.

Example 8

(E)-1-(5,8-dichloro-6,7-dihydroxy-3,4-dihydroiso-quinolin-2(1H)-yl)-3-(5-fluoropyridin-2-yl)but-2-en-1-one

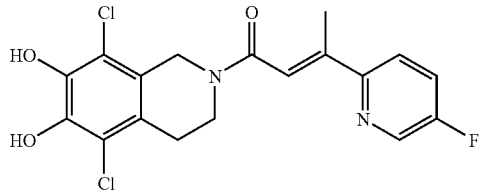

The title compound was obtained from (E)-1-(5,8-dichloro-6,7-dimethoxy-3,4-dihydroisoquinolin-2(1H)-yl)-3-(5-fluoropyridin-2-yl)but-2-en-1-one as an off-white solid in 40% yield (SiO$_2$, Pet. Ether/EtOAc 4/6→4/6+10% EtOH).

$^1$H NMR (CDCl$_3$) rot. mix. δ 8.48 (d, J=3.2 Hz, 1H) 7.56-7.49 (m, 1H) 7.47-7.38 (m, 1H) 7.05 (ma) (s, 1H) 7.01 (mi) (s, 1H) 4.79 (ma) (s, 2H) 4.64 (mi) (s, 2H) 3.95 (mi) (t, J=6.0 Hz, 2H) 3.80 (ma) (t, J=6.0 Hz, 2H) 2.91-2.82 (m, 2H) 2.33 (ma) (s, 3H) 2.28 (mi) (s, 3H).

Example 9

(E)-6,7-dihydroxy-5,8-dimethyl-1,2,3,4-tetrahydroisoquinoline 3-(6-(trifluoromethyl)pyridin-3-yl)acrylamide

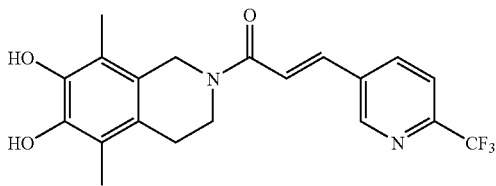

(E)-6,7-Dimethoxy-5,8-dimethyl-1,2,3,4-tetrahydroisoquinoline 3-(6-(trifluoromethyl)pyridin-3-yl)acrylamide (190 mg, 0.45 mmol) was dissolved in dichloromethane (13 mL) and cooled to 0° C. Boron tribromide (1.49 ml, 1.49 mmol, 1M in dichloromethane) was added slowly. The resulting suspension was stirred at 0° C. for 15 minutes, then at rt for 3.5 h and finally refluxed for 1.5 h. The reaction was cooled, quenched with MeOH (5 mL) and evaporated. The residue was dissolved in MeOH (15 mL), neutralized with NaHCO$_3$ (57 mg, 0.68 mmol) and evaporated. The product was purified by flash chromatography using Pet. Ether/EtOAc/MeOH (4/6/1) as eluent to give 165 mg (93%) of (E)-6,7-dihydroxy-5,8-dimethyl-1,2,3,4-tetrahydroisoquinoline 3-(6-(trifluoromethyl)pyridin-3-yl)acrylamide as a reddish mass. $^1$H NMR (CD$_3$OD) rot. mix. δ 8.93 (s, 1H) 8.31 (d, J=8 Hz, 1H) 7.82 (d, J=8 Hz, 1H) 7.63 (m, 1H) 7.51 (d, J=16 Hz) 4.70 (mi) (s, 2H) 4.63 (ma) (s, 2H) 3.93 (ma) (br t, 2H) 3.85 (mi) (br t, 2H) 2.77 (ma) (br t, 2H) 2.69 (mi) (br t, 2H) 2.12 (s, 3H) 2.08 (s, 3H). TLC (Pet. Ether/EtOAc/MeOH 5/5/1) R$_f$ 0.58.

Example 10

(E)-1-(5,8-dichloro-6,7-dihydroxy-3,4-dihydroiso-quinolin-2(1H)-yl)-3-(2-(piperidin-1-yl)-6-(trifluoromethyl)pyridin-3-yl)prop-2-en-1-one

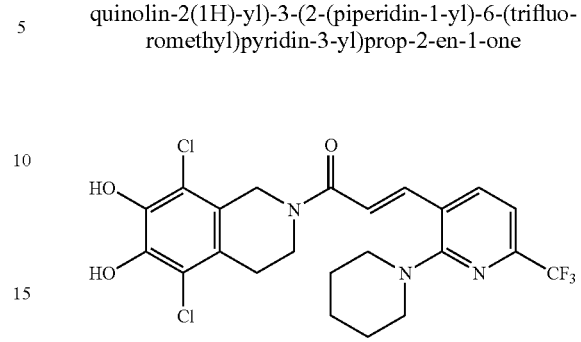

NaOH (1.0 M aq., 2.9 ml, 2.9 mmol) was added to a solution of (E)-methyl 3-(2-(piperidin-1-yl)-6-(trifluoromethyl)pyridin-3-yl)acrylate (181 mg, 0.58 mmol) in THF/EtOH 1/1 (6 mL). The mixture was stirred for 24 h at rt. The solution was diluted with water and acidified with 1M HCl. The precipitate was collected through filtration, dried under vacuum and used directly in the next step.

(E)-3-(2-(piperidin-1-yl)-6-(trifluoromethyl)pyridin-3-yl)acrylic acid (150.0 mg, 0.50 mmol) was suspended in dry THF (7.0 mL). DMAP (111.4 mg, 0.91 mmol) and caesium carbonate (296.0 mg, 0.91 mmol) were added and the mixture was stirred at rt for 15 minutes. 5,8-Dichloro-6,7-dihydroxy-1,2,3,4-tetrahydroisoquinoline hydrobromide (143.0 mg, 0.45 mmol), EDC.HCl (130.6 mg, 0.68 mmol), HOBt (69.8 mg, 0.45 mmol) were then added. The mixture was stirred at rt overnight. Water (100 mL) was added and the product extracted with EtOAc. Combined organic extracts were dried (MgSO$_4$), filtered and concentrated. Purification was done first using flash column chromatography (CH$_2$Cl$_2$/MeOH 98/2→95/5) and then by size exclusion (Sephadex LH20; CHCl$_3$/MeOH 1/1) to yield 55.0 mg (24%) of the title product.

$^1$H NMR (CD$_3$OD) rot. mix. δ 8.11 (ma) (d, J=7.2 Hz, 1H) 8.05 (mi) (d, J=7.2 Hz, 1H) 7.66 (m, 1H) 7.30 (bs, 1H), 7.26 (d, J=7.6 Hz, 1H) 4.79 (mi) (s, 2H) 4.74 (ma) (s, 2H) 3.97 (ma) (br t, 2H) 3.90 (mi) (br t, 2H) 3.26 (m, 4H) 2.88 (ma) (br t, 2H) 2.81 (mi) (br t, 2H) 1.68 (m, 6H).

HRMS (ESI) calc for C$_{23}$H$_{23}$N$_3$O$_3$Cl$_2$ [M+H] 516.1069, found 516.1116.

Example 11

(E)-1-(5,8-dichloro-6,7-dihydroxy-3,4-dihydroiso-quinolin-2(1H)-yl)-3-(2-methyl-6-(trifluoromethyl)pyridin-3-yl)prop-2-en-1-one

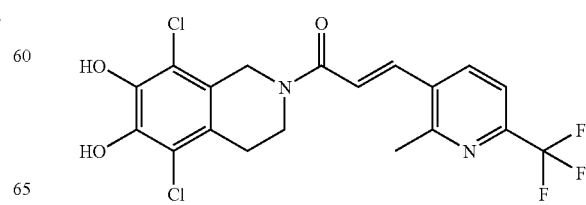

5,8-Dichloro-1,2,3,4-tetrahydroisoquinoline-6,7-diol hydro bromide (183 mg, 0.58 mmol), (E)-3-(2-methyl-6-(trifluoromethyl)pyridin-3-yl)acrylic acid (140 mg, 0.64 mmol), EDC.HCl (167 mg, 0.87 mmol), HOBt (89 mg, 0.58 mmol), DMAP (147 mg, 1.2 mmol) and $Cs_2CO_3$ (391 mg, 1.2 mmol) were suspended in DMF (15 mL) and stirred at rt for 12 h. The reaction mixture was then diluted with water (30 mL) and extracted with EtOAc (3×30 mL). Combined organics were washed with $NaHCO_3$ (2×30 mL, sat. aq.), water (3×30 mL) and brine and dried ($MgSO_4$). After filtration and evaporation the residue was purified by column chromatography ($SiO_2$, $CH_2Cl_2$:MeOH 95:5) and was then further purified by size exclusion chromatography (sephadex, $CHCl_3$:MeOH 1:1) to give the title compound (28 mg, 63 μmol, 11%) as a yellow solid.

$^1$H NMR ($CD_3OD$) rot. mix. δ 8.33 (ma) (d, J=8.0 Hz, 1H) 8.28 (mi) (d, J=8.0 Hz, 1H) 7.88 (ma) (d, J=15.6 Hz, 1H) 7.84 (mi) (d, J=15.6 Hz, 1H) 7.67 (d, J=8.0 Hz, 1H) 7.35 (ma) (d, J=15.6 Hz, 1H) 7.29 (mi) (d, J=15.6 Hz, 1H) 4.81 (mi) (s, 2H) 4.76 (ma) (s, 2H) 3.98 (ma) (t, J=6.0 Hz, 2H) 3.92 (mi) (t, J=6.0 Hz, 2H) 2.91 (ma) (t, J=5.6 Hz, 2H) 2.84 (mi) (t, J=5.6 Hz, 2H) 2.70 (s, 3H).

HRMS (ESI) calc for $C_{19}H_{16}Cl_2F_3N_2O_3$ [M+H] 447.0490, found 447.0550.

Example 12

(E)-1-(5,8-dichloro-6,7-dihydroxy-3,4-dihydroisoquinolin-2(1H)-yl)-3-(6-(trifluoromethyl)pyridin-3-yl)prop-2-en-1-one

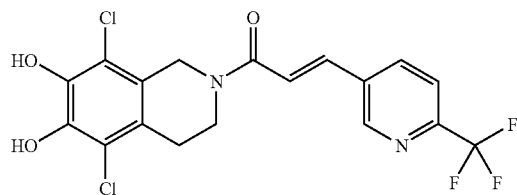

To a solution of CDI (83 mg, 0.51 mmol) in EtOAc (2 mL) was added (E)-3-(6-(trifluoromethyl)pyridin-3-yl)acrylic acid (100 mg, 0.46 mmol). The resulting mixture was heated at reflux for 1 h after which HOBt (35 mg, 0.23 mmol) and 5,8-dichloro-1,2,3,4-tetrahydroisoquinoline-6,7-diol hydro bromide (145 mg, 0.46 mmol) were added. Heating at reflux was continued for 3 h before the reaction mixture was allowed to cool to rt. It was then poured into water (15 mL) and the water-phase was extracted with EtOAc (3×15 mL). Combined organics were washed with water (10 mL) and brine (10 mL) and dried ($MgSO_4$). After filtration and evaporation, the crude was purified by column chromatography ($SiO_2$, EtOAc:petroleum ether 50:50) to give a bright yellow solid which was purified further by precipitating the product in EtOAc via addition of petroleum ether. After decantation of the solvent and drying, the title compound (110 mg, 0.25 mmol, 55%) was obtained as a light reddish solid.

$^1$H NMR ($CD_3OD$) rot. mix. δ 8.98 (ma) (s, 1H) 8.94 (mi) (s, 1H) 8.36-8.33 (m, 1H) 7.87-7.83 (m, 1H) 7.71-7.63 (m, 1H) 7.57-7.52 (m, 1H) 4.82 (mi) (s, 2H) 4.76 (ma) (s, 2H) 3.99 (ma) (t, J=6.0 Hz, 2H) 3.91 (mi) (t, J=6.0 Hz, 2H) 2.92 (ma) (t, J=6.0 Hz, 2H) 2.83 (mi) (t, J=6.0 Hz, 2H).

HRMS (ESI) calc for $C_{18}H_{14}Cl_2F_3N_2O_3$ [M+H] 433.0334, found 433.0338.

Example 13

(E)-1-(5,8-dichloro-6,7-dihydroxy-3,4-dihydroisoquinolin-2(1H)-yl)-3-(6-(trifluoromethyl)pyridin-3-yl)but-2-en-1-one

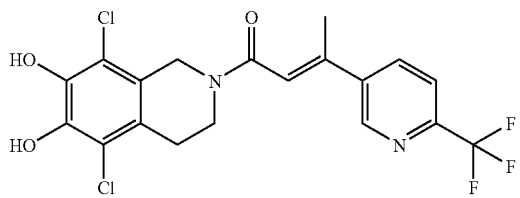

To a solution of 3-(6-(trifluoromethyl)pyridin-3-yl)but-2-enoic acid (2.4 g, 10 mmol) in EtOAc (24 mL) was added CDI (1.7 g, 11 mmol). After heating at reflux for 1 h, TLC ($CH_2Cl_2$:MeOH 9:1) confirmed 3-(6-(trifluoromethyl)pyridin-3-yl)but-2-enoic acid to be consumed. Then 5,8-Dichloro-1,2,3,4-tetrahydroisoquinoline-6,7-diol hydro bromide (3.1 g, 9.7 mmol) was added and the mixture was heated at reflux over night. After cooling to rt the mixture was diluted with EtOAc (24 mL) and the remaining solids were dissolved with small amounts of 1M HCl (aq.). The water and organic phases were separated and the water phase neutralized by addition of 1M NaOH (aq.). The product, which precipitated as a sticky solid, was extracted with EtOAc (5×24 mL, difficult extraction). Combined organics were washed with sat. $NaHCO_3$ (aq.), water and brine and dried ($MgSO_4$). Crude title compound (3.6 g) was purified twice by column chromatography ($SiO_2$, $CH_2Cl_2$:MeOH 98:2) (amount title compound after second chromatography: 1.95 g). Then the product was washed with MeOH repeatedly to yield pure title compound (1.0 g, 2.3 mmol, 23% (pure E-isomer, the Z-isomer could not be isolated)) as a light yellow solid.

$^1$H NMR ($CD_3OD$) rot. mix. δ 8.92 (ma) (d, J=2.0 Hz, 1H) 8.88 (mi) (d, J=1.6 Hz, 1H) 8.21 (ma) (dd, J=2.0, 8.4 Hz, 1H) 8.17 (mi) (dd, J=2.0, 8.4 Hz, 1H) 7.84 (d, J=8.4 Hz, 1H) 6.72 (ma) (br s, 1H) 6.70 (mi) (br s, 1H) 4.72 (ma) (s, 2H) 4.66 (mi) (s, 2H) 3.91 (mi) (t, J=6.0 Hz, 2H) 3.82 (ma) (t, J=6.0 Hz, 2H) 2.87-2.82 (m, 2H) 2.29 (ma) (d, J=1.2 Hz, 3H) 2.19 (mi) (d, J=1.0 Hz, 3H).

HRMS (ESI) calc for $C_{19}H_{16}Cl_2F_3N_2O_3$ [M+H] 447.0490, found 447.0374.

BIOLOGICAL EXAMPLES

Biological Example 1

The remaining contraction, after pre-treatment with various compound examples at a concentration of 10 μM, of human bronchiols after Leukotriene D4 (10 nM) induced contraction according to the in vitro method described herein above are tabulated below.

| Structure | Example number | Remaining contraction (%) |
|---|---|---|
| (structure 1) | 1 | 41 |
| (structure 2) | 2 | 44 |
| (structure 3) | 3 | 24 |
| (structure 5) | 5 | 31 |
| (structure 7) | 7 | 71 |
| (structure 8) | 8 | 76 |
| (structure 9) | 9 | 75 |

| Structure | Example number | Remaining contraction (%) |
|---|---|---|
| [Structure: dichloro-dihydroxy tetrahydroisoquinoline with acyl linker to 2-methyl-6-trifluoromethylpyridine] | 11 | 9 |
| [Structure: dichloro-dihydroxy tetrahydroisoquinoline with acyl linker to 6-trifluoromethylpyridine] | 12 | 6 |
| [Structure: dichloro-dihydroxy tetrahydroisoquinoline with α-methyl acyl linker to 6-trifluoromethylpyridine] | 13 | 7 |

Biological Example 2

The remaining contraction, after pre-treatment with various compound examples at a concentration of 10 µM, of human bronchiols or rat bronhi after the induction of contraction by treatment with the contractile agents acetylcholine (100 uM), carbachol (10 uM), histamine (100 uM), methacholine (100 uM) or a mixture of acetylcholine (100 uM), leukotriene D4 (LTD4) (0.01 uM) and histamine (100 uM), according to the in vitro method described herein above, are tabulated below:

| CONTRACTILE AGENT [concentration (uM)] | SPECIES | COMPOUND (EXAMPLE NUMBER) | REMAINING CONTRACTION (%) |
|---|---|---|---|
| Acetylcholine (100 uM) | human | 12 | 4 |
|  |  | 13 | 7 |
|  | rat | 12 | 40 |
|  |  | 13 | 52 |
| Carbachol (10 uM) | human | 12 | 10 |
|  | rat | 12 | 27 |
| Histamine (100 uM) | human | 12 | 1 |
|  |  | 13 | 3 |
| Methacholine (100 uM) | human | 12 | 7 |
|  | rat | 12 | 49 |
| Mixture of Acetylcholine (100 uM), LTD4 (0.01 uM) and histamine (100 uM) | human | 3 | 43 |
|  |  | 11 | 25 |
|  |  | 12 | 12 |
|  |  | 13 | 18 |

Biological Example 3

Human Peripheral Blood Mononuclear Cell (PBMC) In Vitro Model

Cryopreserved PBMC's (SeraCare, # 72001) were thawed, washed with culture media (RPMI-1640 from Invitrogen, # 61870-036+10% heat inactivated fetal bovine serum from Invitrogen, # 10082-147+100 U/ml penicillin+100 m/ml streptomycin) and tested for viability using Trypan blue (PBMC viability=96%). Cells were then resuspended to $1 \times 10^6$ cells/ml in culture media and 0.5 ml was plated into 24 well culture plates ($5 \times 10^5$ cells/well) before incubation for 30 minutes at 37° C. with 5% CO2 prior to addition of a compound of the present invention (10 µM) or dexamethasone (1 µM). One hour thereafter, LPS (0.1 µg/ml, *Salmonella abortus* equi, Sigma, # L1887) was added and the cells were incubated for another 24 h before collection of the cell culture supernatants, which were assayed for the presence of MCP-1 and LTB4.

MCP-1 levels were quantified employing a Luminex-based assay according the manufacturer's instructions. Data was collected using a Luminex 100 (Luminex Corporation, Austin, Tex.). Standard curves were generated using a 5-parameter logistic curve fitting equation weighted by 1/y (StarStation V 2.0; Applied Cytometry Systems, Sacramento, Calif.). Each sample reading was interpolated from the appropriate standard curve. Calculated concentrations were multiplied by the appropriate dilution factor when necessary.

LTB4 levels were quantified by ELISA following the manufacturer's instructions. Absorbance readings were detected using a ThermoMax microplate reader (Molecular Devices). Standard curves were generated using a 4-parameter logistic curve fitting equation (SoftMax Pro 4.7.1; Molecular Devices). Each sample reading was interpolated from the appropriate standard curve. Duplicate interpolated sample values were averaged and standard deviations were calculated. Calculated concentrations were multiplied by the appropriate dilution factor.

The inhibitory effect of compounds of the present invention, dexamethasone, and vehicle on production of MCP-1 and LTB4 in the PBMC model as described herein above, with (+LPS) or without (−LPS) LPS-induced mediator production, is tabulated below.

| Compound | Mean MCP-1 (pg/ml) | Standard deviation (MCP-1) | Mean LTB-4 (pg/ml) | Standard deviation (LTB-4) |
| --- | --- | --- | --- | --- |
| Vehicel (−LPS) | 133.5 | 19.2 | 2.9 | 0.5 |
| Vehicel (+LPS) | 858.2 | 25.5 | 30.4 | 1.5 |
| Example 12 (−LPS) | 229.7 | 60.9 | 3.9 | 0.2 |
| Example 12 (+LPS) | 303.1 | 94.3 | 9.9 | 2.3 |
| Example 13 (−LPS) | 217.1 | 45.7 | 4.3 | 0.2 |
| Example 13 (+LPS) | 256.7 | 11.5 | 9.8 | 0.8 |
| Dexamethasone (−LPS) | 0 | 0 | 2.7 | 0.7 |
| Dexamethasone (+LPS) | 1425.6 | 193.8 | 12.6 | 0.3 |

The invention claimed is:

1. A compound according to formula I

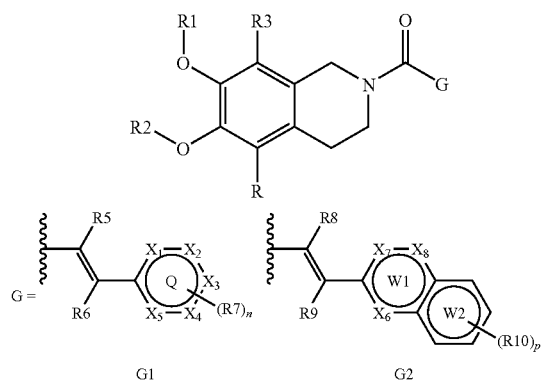

wherein

R1 is selected from H and methyl;
R2 is selected from H and methyl;
R3 is selected from H, fluoro, chloro, bromo, C1-3 alkyl and CH2 phenyl;
R4 is selected from H, fluoro, chloro, bromo, C1-3 alkyl and CH2 phenyl;
G is selected from G1 and G2;
in G1 the stereochemistry of the double-bond of G1, onto which the substituents R5 and R6 are attached, is such that R5 and R6 are oriented in a cis-fashion, or in a trans-fashion, relative to each other;
R5 is selected from H, C1-5 alkyl, CH2 phenyl and C1-5 fluoroalkyl;
R6 is selected from H, C1-5 alkyl, CH2 phenyl and C1-5 fluoroalkyl;
X1, X2, X3, X4 and X5 are, independently of each other, selected from N and C; 0 (zero), 1 or 2 of X1, X2, X3, X4 and X5 is N; Q is optionally substituted with a maximum of "n" independently selected substituent(s) R7 at any substitutable ring carbon atom, wherein "n" represents an integer number;

the integer number "n" is 0 to 2;
R7 is selected from C1-5 alkyl, C1-5 fluoroalkyl, halo, hydroxy, C0-3 alkyleneOC0-5 alkyl, C0-3 alkyleneOC1-5 fluoroalkyl, C0-3 alkyleneNH2, C0-3 alkyleneNHC1-3 alkyl, C0-3 alkyleneN(C1-5 alkyl)2, in which the C1-5 alkyl may be the same or different, N(C4-5 alkylene), C1-5 alkylthio, S(O)C 1-5 alkyl, SO2C 1 -5 alkyl, C1-5 fluoroalkylthio, NH(CO)C1-5 alkyl, NH(CO)C 1 -5 alkoxy, NHSO2C1-5 alkyl, (CO)C1-5 alkyl, COOH, (CO)C1-5 alkoxy, (CO)NH2, (CO)NHC1-5 alkyl, (CO)N(C1-5 alkyl)2, in which the C1-5 alkyl may be the same or different, cyano, SO2NHC0-5 alkyl, nitro, aryl, heteroaryl, azido (N3), and morpholinyl;
in G2 the stereochemistry of the double-bond of G2, onto which the substituents R8 and R9 are attached, is such that R8 and R9 are oriented in a cis-fashion, or in a trans-fashion, relative to each other;
R8 is selected from H, C1-5 alkyl, CH2 phenyl and C1-5 fluoroalkyl;
R9 is selected from H, C1-5 alkyl, CH2 phenyl and C1-5 fluoroalkyl;
the condensed rings W1 and W2 together represent a bicyclic aromatic system, in which X6, X7 and X8, independently of each other, are selected from N and C; none or one of X6, X7 and X8 is N; said bicyclic aromatic system is optionally substituted with a maximum of "p" independently selected substituent(s) R10, at any substitutable ring carbon atom of any of the rings W1 and W2, wherein "p" represents an integer number;
The integer number "p" is 0 to 2;
R10 is selected from C1-5 alkyl, C1-5 fluoroalkyl, halo, hydroxy, C0-3 alkyleneOC0-5 alkyl, C0-3 alkyleneOC1-5 fluoroalkyl, C0-3 alkyleneNH2, C0-3 alkyleneNHC1-3 alkyl, C0-3 alkyleneN(C 1-5 alkyl)2, in which the C1-5 alkyl may be the same or different, N(C4-5 alkylene), C1-5 alkylthio, S(O)C1-5 alkyl, SO2C1-5 alkyl, C1-5 fluoroalkylthio, NH(CO)C1-5 alkyl, NH(CO)C1-5 alkoxy, NHSO2C1-5 alkyl, (CO)C1-5 alkyl, COOH, (CO)C1-5 alkoxy, (CO)NH2, (CO)NHC1-5 alkyl, (CO)N(C1-5 alkyl)2, in which the C1-5 alkyl may be the same or different, cyano, SO2NHC0-5 alkyl, nitro, aryl, heteroaryl, azido (N3), and morpholinyl;
as a free base, an acid in its non-charged protonated form or a pharmaceutically acceptable salt, and as a pure stereoisomer, a racemic-diastereomeric-or scalemic mixture; with the proviso
that not both of R1 and R2 is methyl.

2. The compound according to claim 1, wherein R1 and R2 is H.

3. The compound according to claim 2, wherein R3 and R4, independent of each other, are selected from H, fluoro, chloro, bromo, and methyl.

4. The compound according to claim 3, wherein R3 and R4 are chloro.

5. The compound according to claim 1, wherein G is G1 and the stereochemistry of the double-bond of G1, onto which the substituents R5 and R6 are attached, is such that R5 and R6 are oriented in a trans-fashion relative to each other.

6. The compound according to claim 1, wherein G is G1 and at least one of X1 to X5 is N.

7. The compound according to claim 6, wherein G is G1, X1 or X2 is N and only one of X1 to X5 is N.

8. The compound according to claim 1, wherein G is G1, "n" is 1 or 2, and R7 is selected from C1-C3 alkyl, trifluoromethyl, halo, hydroxy, N(C4-5 alkylene), methoxy, SO2Me, cyano, thienyl, nitro, phenyl, morpholinyl and NMe2.

9. The compound according to claim 8, wherein R7 is selected from methyl, trifluoromethyl, fluoro, chloro and NMe2.

10. The compound according to claim 1 wherein G is G1 and R5 is H.

11. The compound according to claim 1, wherein G is G1 and R6 is H or methyl.

12. The compound according to claim 1, wherein G is G2 and the stereochemistry of the double-bond of G2, onto which the substituents R8 and R9 are attached, is such that R8 and R9 are oriented in a trans-fashion relative to each other.

13. The compound according to claim 12, wherein G is G2, at least one of X6 to X8 is N.

14. The compound according to claim 12, wherein G is G2 and R8 and R9 are, independently or each other, selected from H and methyl.

15. The compound according to claim 1, wherein said compound is selected from the group consisting of:

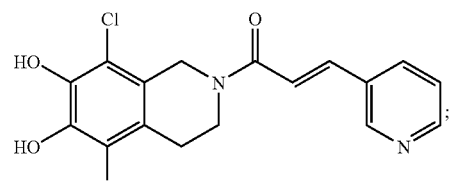

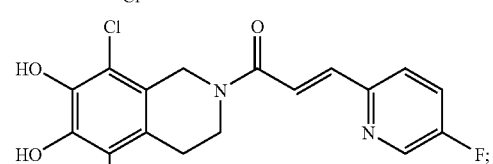

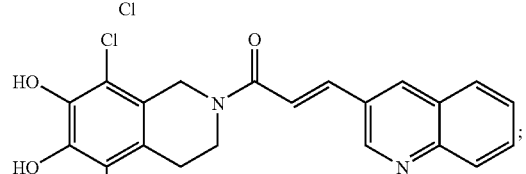

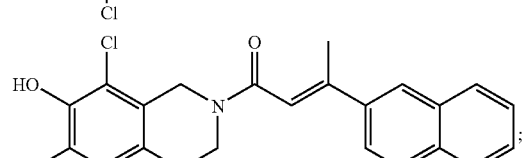

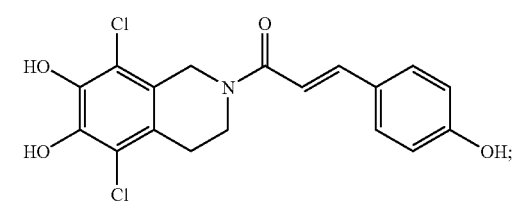

-continued

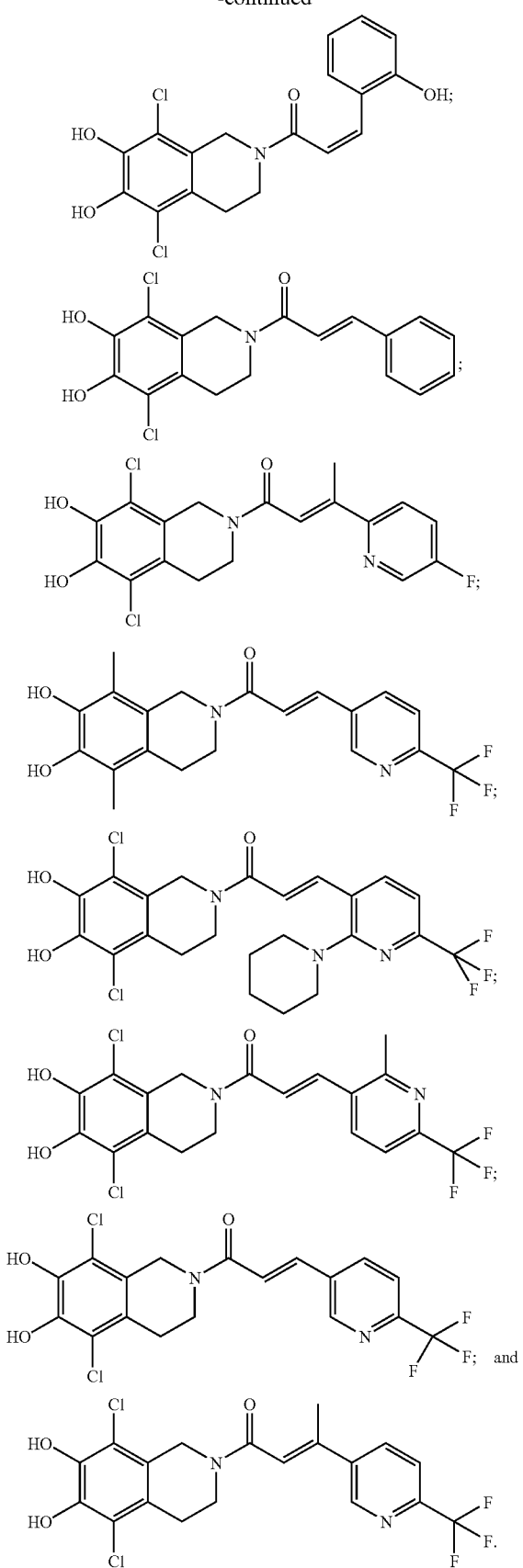

16. The compound according to claim 1, wherein said compound is selected from the group consisting of:

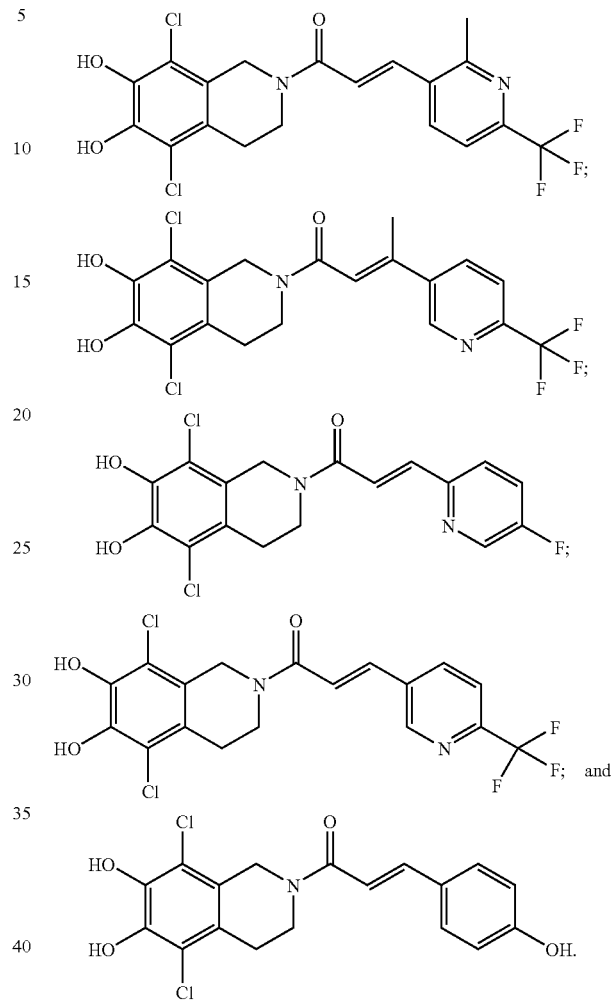

17. A pharmaceutical composition comprising a compound according to claim 1 and at least one pharmaceutically acceptable carrier.

18. The pharmaceutical composition according to claim 17, comprising an anti-asthmatic.

19. The pharmaceutical composition according to claim 18, wherein the principal mechanism of action of the anti-asthmatic is selected from the group consisting of β2-agonist, anticholinergic and calcium antagonist, or wherein the anti-asthmatic is a corticosteroid.

20. A method of prevention and/or treatment of a disease or condition characterized by bronchoconstriction and/or inflammatory conditions of the respiratory apparatus, comprising administering to a mammal, in need of such prevention and/or treatment, a therapeutically effective amount of a compound according to claim 1.

21. The method according to claim 20 further comprising the simultaneous or consecutive administration of a therapeutically effective amount an anti-asthmatic.

22. The method according to claim 21, wherein the administered dose of the anti-asthmatic is 1 to 10 times less than the established therapeutically effective dose when administered alone for prevention or treatment of the same disease or condition.

23. The method according to claim 21, wherein the administered dose of a compound is 1 to 10 times less than the established therapeutically effective dose when administered alone for prevention or treatment of the same disease or condition.

24. The method according to claim 21, wherein the principal mechanism of action of the anti-asthmatic is selected from the group consisting of β2-agonist, anticholinergic and calcium antagonist, or wherein the anti-asthmatic is a corticosteroid.

25. The method according to claim 20, wherein the disease comprises as asthma, chronic obstructive pulmonary disease, chronic bronchitis, emphysema, bronchiectasis, cystic fibrosis, bronchiolitis and/or bronchopulmonary dysplasia.

* * * * *

UNITED STATES PATENT AND TRADEMARK OFFICE
CERTIFICATE OF CORRECTION

PATENT NO. : 8,318,768 B2
APPLICATION NO. : 12/668599
DATED : November 27, 2012
INVENTOR(S) : Dalence et al.

It is certified that error appears in the above-identified patent and that said Letters Patent is hereby corrected as shown below:

In the Claims:

At Column 41, Lines 51-67, claim 1, please replace formula I with the one below:

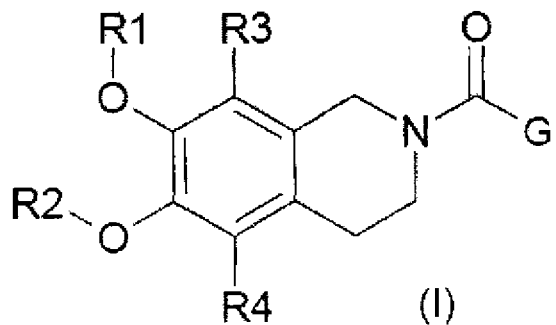

Signed and Sealed this
Thirtieth Day of July, 2013

Teresa Stanek Rea
*Acting Director of the United States Patent and Trademark Office*